United States Patent

Takano

(10) Patent No.: US 9,757,070 B2
(45) Date of Patent: Sep. 12, 2017

(54) BIOLOGICAL INFORMATION MEASUREMENT APPARATUS, INFORMATION PROCESSING APPARATUS, AND BIOLOGICAL INFORMATION MEASUREMENT SYSTEM

(71) Applicant: Seiko Epson Corporation, Shinjuku-ku (JP)

(72) Inventor: Yuichi Takano, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 287 days.

(21) Appl. No.: 14/575,904

(22) Filed: Dec. 18, 2014

(65) Prior Publication Data

US 2015/0173614 A1 Jun. 25, 2015

(30) Foreign Application Priority Data

Dec. 25, 2013 (JP) ................................. 2013-266629

(51) Int. Cl.
*A61B 5/00* (2006.01)
*G06F 11/00* (2006.01)
(Continued)

(52) U.S. Cl.
CPC ............ *A61B 5/6898* (2013.01); *A61B 5/681* (2013.01); *G06F 11/00* (2013.01); *G06F 19/3418* (2013.01); *H04L 67/125* (2013.01); *H04L 67/303* (2013.01); *H04L 67/325* (2013.01); *H04W 4/008* (2013.01); *A61B 5/02055* (2013.01); *A61B 5/112* (2013.01); *A61B 5/165* (2013.01); *A61B 5/4806* (2013.01); *A61B 5/4866* (2013.01)

(58) Field of Classification Search
CPC . A61B 5/00; G06F 11/00; G06F 19/11; G06F 19/00; H04L 67/00
See application file for complete search history.

(56) References Cited

U.S. PATENT DOCUMENTS

2005/0233789 A1* 10/2005 Maekawa ............... H04L 12/12
 463/1
2005/0246748 A1* 11/2005 Muroi .............. H04N 21/23418
 725/90

(Continued)

OTHER PUBLICATIONS

Bluetooth. Printed Dec. 15, 2014 (w/ English translation). https://www.bluetooth.org/ja-jp/specification/adopted-specifications. (nine pages).

*Primary Examiner* — Andrew Lai
*Assistant Examiner* — Sumitra Ganguly
(74) *Attorney, Agent, or Firm* — Kilpatrick Townsend & Stockton LLP

(57) ABSTRACT

A biological information measurement apparatus includes a sensor unit, a processing unit which detects biological information based on sensor information from the sensor unit, a communication unit which transmits the biological information to an information processing apparatus, and a time output unit which outputs time. The communication unit obtains a delay time of the transmission timing of the biological information based on apparatus-specific information, obtains a first transmission timing based on the time output from the time output unit, and transmits the biological information at a second transmission timing delayed from a first transmission timing by the obtained delay time.

19 Claims, 16 Drawing Sheets

(51) Int. Cl.
*G06F 19/00* (2011.01)
*H04L 29/08* (2006.01)
*H04W 4/00* (2009.01)
A61B 5/11 (2006.01)
A61B 5/16 (2006.01)
A61B 5/0205 (2006.01)

(56) References Cited

U.S. PATENT DOCUMENTS

2006/0220839 A1* 10/2006 Fifolt .................. A61B 5/0002
　　　　　　　　　　　　　　　　　　340/539.12
2008/0076978 A1* 3/2008 Ouchi ..................... A61B 5/00
　　　　　　　　　　　　　　　　　　600/301

* cited by examiner

BIOLOGICAL INFORMATION MEASUREMENT APPARATUS, INFORMATION PROCESSING APPARATUS, AND BIOLOGICAL INFORMATION MEASUREMENT SYSTEM

This application claims priority to Japanese Patent Application No. 2013-266629, filed Dec. 25, 2013, the entirety of which is hereby incorporated by reference.

BACKGROUND

1. Technical Field

The present invention relates to a biological information measurement apparatus, an information processing apparatus, a biological information measurement system, and the like.

2. Related Art

Recently, Bluetooth (Registered Trademark) Low Energy (abbreviated as BLE) has been established, and a smart device (client, peripheral) and a health care device (server, host) can be simply connected together in a power saving manner. Unlike the Bluetooth profile in the related art, in BLE, a profile specialized for a specific use (exercise, health, smartphone cooperation, or the like) is established, and if the profile corresponds to the established standard profile, interconnection between different pieces of equipment is secured.

Various articles in which the specification of BLE is defined are disclosed on a Web page represented by a URL described in https://www.bluetooth.org/ja-jp/specification/adopted-specifications.

When a user measures and analyzes biological information of daily life or during exercise using a health care-related service, in a service in which the state of the user, such as the stress state or the sleep state of the user, is determined based on biological information measured by a health care device and accumulated for a predetermined period of time, after the biological information is transmitted from the health care device to the smart device, the biological information is transmitted from the smart device to a server. On this occasion, since each smart device performs upload to the server at the same timing, load concentration onto the server occurs, and there is a risk of the occurrence of significant failure.

SUMMARY

An aspect of the invention relates to a biological information measurement apparatus including a sensor unit, a processing unit which detects biological information based on sensor information from the sensor unit, a communication unit which transmits the biological information to an information processing apparatus, and a time output unit which outputs time. The communication unit obtains a delay time of the transmission timing of the biological information based on apparatus-specific information, obtains the first transmission timing based on the time output from the time output unit, and transmits the biological information at a second transmission timing delayed from the first transmission timing by the obtained delay time.

In the aspect of the invention, the communication unit of the biological information measurement apparatus transmits the biological information at the second transmission timing delayed from the first transmission timing by the obtained delay time. Then, the communication unit of the information processing apparatus receives the biological information at the second transmission timing delayed from the first transmission timing by the obtained delay time.

With this, it is possible to distribute the timing of transmission of biological information from respective biological information measurement apparatuses to respective information processing apparatuses. As a result, it is possible to distribute the timing of transmission of biological information from the respective information processing apparatuses to a server.

In the aspect of the invention, the biological information measurement apparatus may further include a storage unit which stores the biological information corresponding to time information, and the communication unit may transmit the biological information stored in the storage unit at the second transmission timing.

With this configuration, the information processing apparatus can collectively receive the biological information stored in the storage unit of the biological information measurement apparatus, or the like.

In the aspect of the invention, the processing unit may detect the first biological information and second biological information, which is the biological information, based on the sensor information, and the communication unit may transmit the first biological information in a first communication cycle and may transmit the second biological information in a second communication cycle longer than the first communication cycle.

With this configuration, it is possible to perform the transmission/reception of the first biological information while satisfying real time performance, and to collectively transmit/receive the second biological information at a required timing, or the like.

In the aspect of the invention, the communication unit may divide data of the biological information into a plurality of blocks each having a plurality of packets and may transmit the plurality of blocks.

With this configuration, it is possible to transmit/receive data of a second data amount greater than a first data amount, which is transmittable/receivable based on the standard profile of proximity wireless communication, through proximity wireless communication.

In the aspect of the invention, the communication unit may transmit the plurality of blocks with a first characteristic having a property of read with no acknowledge by proximity wireless communication and may receive the reception results of the blocks in the information processing apparatus with a second characteristic having a property of write with acknowledge.

With this configuration, it is possible to determine the success/failure of the transmission of the plurality of packets only by the reception of a single reception result, or the like.

In the aspect of the invention, the communication unit may change a communication speed from a first communication speed to a second communication speed faster than the first communication speed before transmitting the biological information and may change the communication speed to a third communication speed slower than the second communication speed after the transmission of the biological information is completed.

With this configuration, it is possible to maintain power saving performance even if high-speed transfer is performed, or the like.

In the aspect of the invention, the communication unit may receive a communication speed change instruction with a first characteristic having a property of write with acknowledge by proximity wireless communication, may change the communication speed based on the received communication speed change instruction, and may transmit a communication speed change completion notification with a second characteristic having a property of read with acknowledge.

With this configuration, it is possible to perform communication at the communication speed represented by the received communication speed change instruction, or the like.

In the aspect of the invention, the communication unit may transmit a notification that the biological information is transmittable to the information processing apparatus at the second transmission timing when the biological information is transmittable and may transmit the biological information when a transmission start instruction is received from the information processing apparatus.

With this configuration, it is possible to allow the information processing apparatus to instruct to start transmission to the biological information measurement apparatus, or the like.

In the aspect of the invention, the communication unit may transmit the upload data size of the biological information with a third characteristic having a property of read with acknowledge to the information processing apparatus to start transmission of the biological information when the transmission start instruction is received from the information processing apparatus.

With this configuration, it is possible to give a notification about the start of transmission of data and the upload data size, and to receive that an external apparatus understands the start of transmission, or the like.

In the aspect of the invention, the biological information measurement apparatus may further include a storage unit which stores the biological information in association with a measurement time output from the time output unit at the timing when the biological information is detected.

With this configuration, it is possible to allow the information processing apparatus to specify the measurement time of the received biological information, or the like.

In the aspect of the invention, the biological information may include information regarding at least one of a step count, calorie consumption, calorie intake, mental stress information, sleep information, and behavior analysis information.

With this configuration, it is possible to transmit biological information of a subject to the information processing apparatus, or the like.

Another aspect of the invention relates to an information processing apparatus including a communication unit which performs communication with a biological information measurement apparatus, which detects biological information based on sensor information from a sensor unit and obtains a first transmission timing of the biological information from time, and a processing unit. The communication unit receives the biological information at a second transmission timing delayed from the first transmission timing by a delay time obtained based on apparatus-specific information of the biological information measurement apparatus.

According to this aspect of the invention, the communication unit of the biological information measurement apparatus transmits the biological information at the second transmission timing delayed from the first transmission timing by the obtained delay time. Then, the communication unit of the information processing apparatus receives the biological information at the second transmission timing delayed from the first transmission timing by the obtained delay time.

With this, it is possible to distribute the timing of transmission of the biological information from respective biological information measurement apparatuses to respective information processing apparatuses. As a result, it is possible to distribute the timing of transmission of biological information from the respective information processing apparatuses to a server.

In the aspect of the invention, the processing unit may instruct the biological information measurement apparatus to start transmission of the biological information when the communication unit receives a notification that the biological information is transmittable from the biological information measurement apparatus.

With this configuration, it is possible to allow the communication unit of the biological information measurement apparatus to start transmission of biological information, or the like.

Still another aspect of the invention relates to a biological information measurement system including a biological information measurement apparatus, and an information processing apparatus. The biological information measurement apparatus detects biological information based on sensor information from a sensor unit, obtains a delay time of the transmission timing of the biological information based on apparatus-specific information, and transmits the biological information at a second transmission timing delayed from a first transmission timing obtained based on time by the delay time. The information processing apparatus receives the biological information at the second transmission timing.

According to some aspects of the invention, it is possible to provide a biological information measurement apparatus, an information processing apparatus, a biological information measurement system, and the like capable of distributing the timing of transmission of biological information from respective biological information measurement apparatuses to information processing apparatuses.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
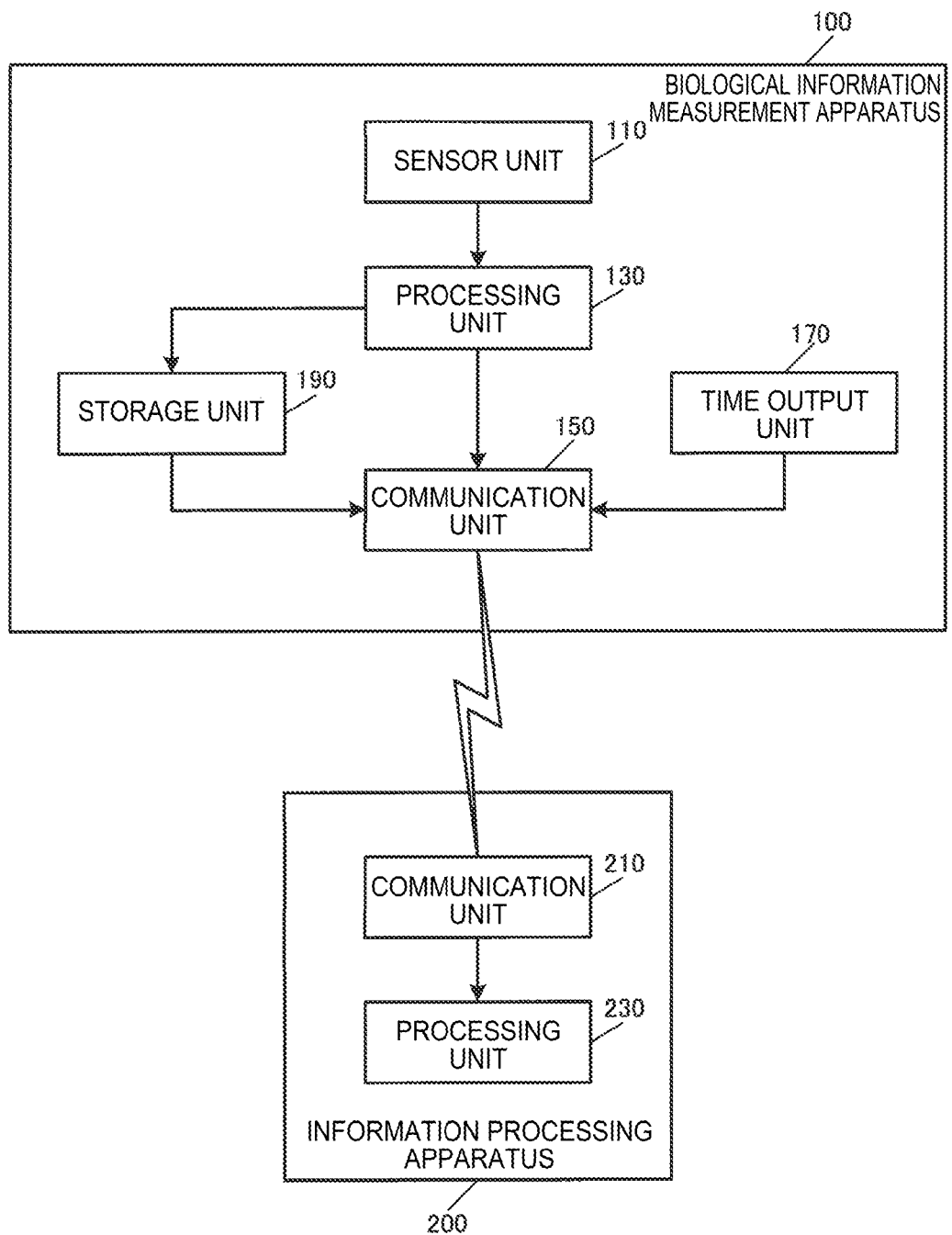
FIG. 1 shows a system configuration example of an embodiment.

Hereinafter, an embodiment will be described. It should be noted that the following embodiment is not intended to limit the content of the invention described in the appended claims. The entire configuration described in the embodiment is not the necessarily essential components of the invention.

1. Outline of Embodiment

A biological information measurement apparatus, an information processing apparatus, a biological information measurement system, and the like of the embodiment enable transmission/reception of data of a second data amount greater than a first data amount, which is transmittable/receivable based on the standard profile of proximity wireless communication, through proximity wireless communication.

In the embodiment, for example, processing when BLE communication is used as proximity wireless communication and transmission/reception of biological information from a health care device (server, host) to a smart device (client, peripheral) is performed will be described. It should be noted that BLE is a communication system which is superior in power saving than proximity wireless communication in the related art. The health care device is one of the above-described biological information measurement apparatuses.

Here, the biological information which is transmitted from the health care device includes first biological information (or first biological data) and second biological information (or second biological data). Specifically, the first biological information is information regarding a pulse, body temperature, blood pressure, a blood glucose level, a step count, calorie consumption, and the like, and has a first data amount. The second biological information is, for example, calorie intake, mental stress information (mental state), behavior analysis information, sleep information, and the like, and has a second data amount greater than the first data amount. Both the first biological information and the second biological information are information which sequentially change. While the first biological information is information which needs to be notified to a user through real-time communication such that the user recognizes the situation of the body (information for which a required response waiting time is short), the second biological information is information (information for which a required response waiting time is long) which may provide information for a predetermined period of time, for example, for every hour, instead of being recognized in real time.

Then, in the standard profile of BLE, since a method which transmits and receives the first biological information is defined, the first biological information can be successively transmitted from the health care device to the smart device to satisfy real-time performance while maintaining power saving performance.

However, in the standard profile of BLE, a method which transmits and receives the other second biological information is not defined. This is because BLE does not assume transmission/reception of data of a comparatively large data amount. For this reason, similarly to the first biological information, when data of the second biological information is successively transmitted, since the second data amount is greater than the first data amount, there is a problem in that it is not possible to maintain power saving performance. The same applies to a case where the first biological information is accumulated for a predetermined period of time, and the accumulated first biological information is transmitted together by BLE.

Accordingly, in the embodiment, only data, such as the first biological information, or summary data for which a required response waiting time is short is successively transmitted in a short cycle using BLE communication, and detailed data, such as the second biological information, is collectively transmitted separately.

Specifically, in the embodiment, in order to transmit data of the second data amount, a specific profile is defined, and transmission/reception of the second biological information is performed based on the specific profile. In the communication based on the specific profile of the embodiment, as described above, instead of successively transmitting the second biological information in the same short communication cycle as the first biological information, the second biological information is recorded in the storage unit of the health care device in association with time information, and data of the second biological information is collectively transmitted every hour.

With this, it is possible to transmit not only the first biological information but also the second biological information from the health care device to the smart device while maintaining power saving performance.

As described above, when communication between the health care device and the smart device is disconnected, there is a problem in that the smart device cannot receive the first biological information detected during disconnection of communication.

Against this problem, in the embodiment, the first biological information detected during disconnection of communication is stored in the storage unit of the health care device, and the non-transmitted first biological information is collectively transmitted based on the specific profile after reconnection. With this, it is possible to prevent the occurrence of acquisition leakage of the first biological information in the smart device.

In the embodiment, while communication is performed based on the specific profile, processing for increasing the communication speed of BLE and returning the communication speed to the communication speed established by the standard profile after transmission/reception is completed is performed. Even when the communication speed is changed, it is possible to transmit the first biological information based on the standard profile as usual. While the second biological information is transmitted based on the specific profile, it is possible to transmit the first biological information based on the standard profile in parallel.

The biological information (second biological information) measured and recorded by the health care device is transmitted from the health care device to the smart device, and is then transmitted from the smart device to a Web server.

On this occasion, since all smart devices which are used in a market perform upload to the Web server at the same timing, load concentration onto the Web server occurs, and there is a risk of the occurrence of significant failure.

Accordingly, in the biological information measurement apparatus, the information processing apparatus, the biological information measurement system, and the like of the embodiment, it is possible to distribute the timing of transmission of the biological information from respective biological information measurement apparatuses to an information processing apparatus.

Hereinafter, an example where the first biological information is transmitted first based on the standard profile and the second biological information is transmitted based on the specific profile will be described. Thereafter, the details of a communication method based on the specific profile of the embodiment will be described.

2. Examples 2.1. System Configuration Example

First, FIG. 1 shows a configuration example of a biological information measurement apparatus 100 and an information processing apparatus 200 of the embodiment, and a biological information measurement system including the same. The biological information measurement apparatus 100 includes a sensor unit 110, a processing unit 130, a communication unit 150, a time output unit 170, and a storage unit 190. The information processing apparatus 200 includes a communication unit 210 and a processing unit 230. It should be noted that the biological information measurement apparatus 100 corresponds to an information processing apparatus 10 of FIG. 6A described below, and the information processing apparatus 200 corresponds to an external apparatus 50 of FIG. 6A described below.

The biological information measurement apparatus 100, the information processing apparatus 200, and the biological information measurement system including the same are not limited to the configuration of FIG. 1, and various modifications may be made by omitting some components, adding other components, or the like. Some or all of the functions of the information processing apparatus 200 may be realized by a server connected to the biological information measurement apparatus 100 or the information processing apparatus 200 through communication.

Next, the respective units of the biological information measurement apparatus 100 will be described.

First, the sensor unit 110 is, for example, a pulse sensor, a temperature sensor, a body motion sensor, and the like. The sensor unit 110 is not limited to a single sensor configuration, and may have a plural-sensor configuration. When the sensor unit 110 has a plurality of sensors, the sensors may be provided at different positions (regions) of the biological information measurement apparatus 100.

The pulse sensor is a sensor for detecting a pulse sensor signal, and for example, a photoelectric sensor or the like is considered. However, the pulse sensor is not limited to the photoelectric sensor, and other sensors, such as a sensor using an ultrasonic wave, may be used.

As the body motion sensor, a motion sensor (acceleration sensor), a pressure sensor (contact pressure sensor), or the like is used. Furthermore, as the body motion sensor, a plurality of sensors may be provided.

Next, the processing unit 130 detects the biological information (first biological information and second biological information) based on sensor information obtained from the sensor unit 110. The processing unit 130 of FIG. 1 corresponds to an information acquisition unit 11 of FIG. 6A described below.

Then, the communication unit 150 transmits the biological information (first biological information and second biological information) to the information processing apparatus 200. It should be noted that the communication unit 150 of FIG. 1 corresponds to a communication unit 13 of FIG. 6A described below. The functions of the processing unit 130 and the communication unit 150 can be realized by hardware, such as various processors (CPU and the like) or an ASIC (gate array or the like), a program, or the like.

The time output unit 170 outputs time. The function of the time output unit 170 is realized using, for example, a hardware timer or the like.

Next, the storage unit 190 stores the biological information (second biological information) corresponding to the time information. The storage unit 190 becomes a work area of the processing unit 130, the communication unit 150, or the like, and the function thereof can be realized by a memory, such as a RAM, an HDD, or the like.

Next, the respective units of the information processing apparatus 200 will be described.

First, the communication unit 210 performs proximity wireless communication with the communication unit 210 of the biological information measurement apparatus 100 to acquire the biological information.

Then, the processing unit 230 performs various kinds of processing based on the biological information received by the communication unit 210 or the like. For example, the processing unit 230 performs processing for causing an external display unit to display the acquired biological information or the like. The functions of the communication unit 210 and the processing unit 230 can be realized by hardware, such as various processors (CPU and the like) or an ASIC (gate array or the like), a program, or the like.

2.2. Details of Processing

In the embodiment, information which is transmitted from the biological information measurement apparatus 100 to the information processing apparatus 200 is the biological information. Then, as described above, the biological information includes the first biological information for which the transmission/reception method is defined in the standard profile of the communication standard (BLE) of proximity wireless communication, and the second biological information for which the transmission/reception method is not defined in the standard profile of the communication standard (BLE).

Figure 2:
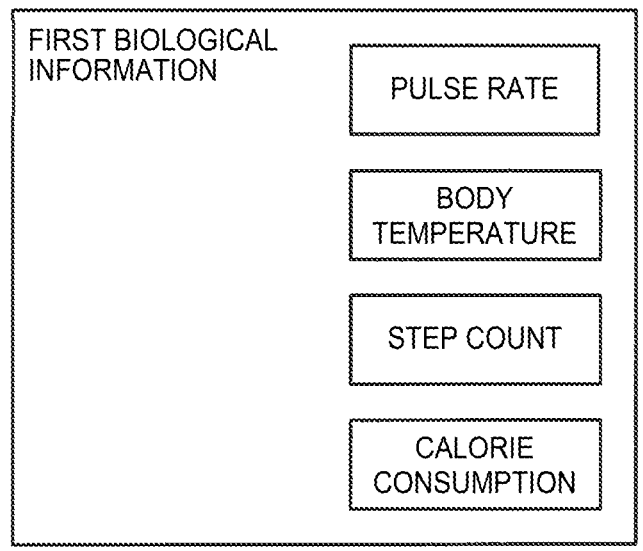
FIG. 2 is an explanatory view of first biological information and second biological information.
Figure 2:
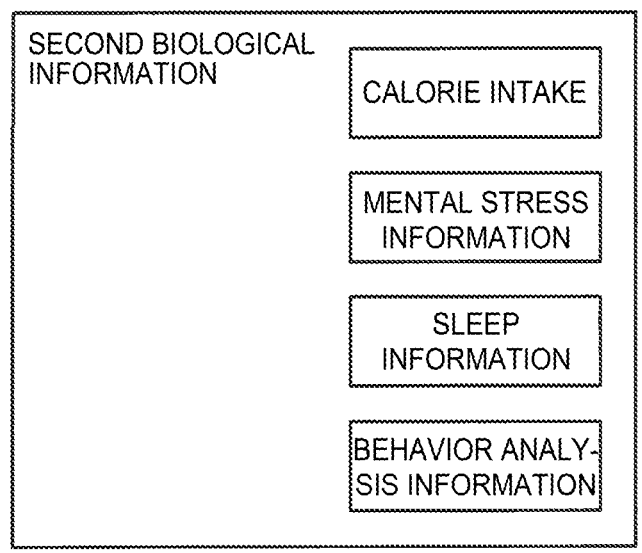

Specifically, as shown in FIG. 2, the first biological information is a pulse rate, body temperature, a step count, calorie consumption, and the like. The second biological information includes information of at least one of calorie intake, mental stress information, sleep information, and behavior analysis information.

With this, it is possible to transmit biological information of a subject to the information processing apparatus 200, or the like.

Then, in the embodiment, the communication unit 150 of the biological information measurement apparatus 100 transmits the first biological information based on the standard profile of the communication standard for communication in the communication unit 150, and transmits the second biological information based on the specific profile of the above-described communication standard.

With this, it is possible to transmit not only the first biological information but also the second biological information which cannot be transmitted by the standard profile.

The communication standard which is used in the embodiment is a proximity wireless communication standard, and the standard profile is a profile which is standardized in the proximity wireless communication standard. Specifically, the proximity wireless communication standard is BLE.

With this, it is possible to perform transmission/reception of the biological information according to the proximity wireless communication standard, or the like. Specifically, it is possible to perform transmission/reception of the first biological information according to the standard profile defined in BLE.

When the biological information measurement apparatus 100 transmits the second biological information to the information processing apparatus 200 according to the specific profile, processing at the time of upload sequence described below is performed. Specifically, as described below in detail referring to FIGS. 7 to 10, the communication unit 150 divides data of the biological information (second biological information) into a plurality of blocks each having a plurality of packets, and transmits a plurality of blocks, for example, in units of blocks.

With this, it is possible to transmit and receive data (data of second biological information) of the second data amount greater than the first data amount, which is transmittable/receivable by the standard profile of the proximity wireless communication, through proximity wireless communication.

The communication unit 150 of the biological information measurement apparatus 100 transmits the first biological information in a first communication cycle and transmits the second biological information stored in the storage unit 190 in a second communication cycle longer than the first communication cycle.

In other words, specifically, the communication unit 150 transmits the first biological information with the first data amount at the (respective) transmission timings of the first communication cycle and transmits the second biological information with the second data amount greater than the first data amount at the (respective) transmission timings of the second communication cycle.

Then, the communication unit 210 of the information processing apparatus 200 receives the first biological information in the first communication cycle and receives the second biological information in the second communication cycle.

With this, it is possible to perform transmission/reception of the first biological information while satisfying real time performance and to collectively transmit/receive the second biological information at a required timing.

Figure 3:
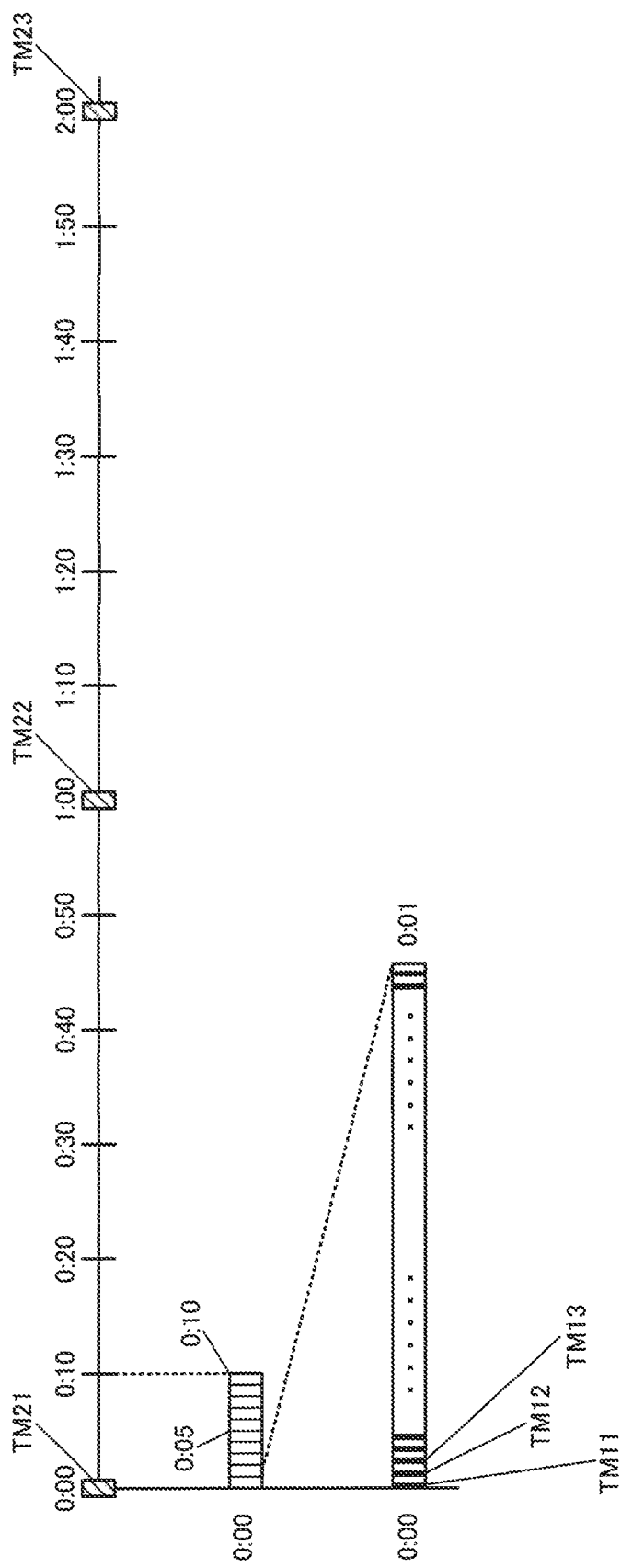
FIG. 3 is an explanatory view of a first communication cycle and a second communication cycle.

A specific example is shown in FIG. 3. FIG. 3 shows each transmission timing of the first communication cycle and each transmission timing of the second communication cycle with the horizontal axis as a time axis. In this example, it is assumed that the first communication cycle is one second and the second communication cycle is one hour.

At this time, in this example, just the time 0:00 is a first transmission timing TM21 of the second communication cycle, and a next second transmission timing TM22 is just the time 1:00 after one hour.

A second section of FIG. 3 shows the time zone of the time 0:00 to the time 0:10 extracted from a first section of FIG. 3, and a third section of FIG. 3 shows the time zone of the time 0:00 to the time 0:01 extracted from the second section of FIG. 3 on an enlarged scale. As shown in the third section of FIG. 3, in this example, just the time 0:00:00 is a first transmission timing TM11 of the first communication cycle, and the time 0:00:01 after one second is a second transmission timing TM12.

In the embodiment, as shown in the example of FIG. 3, the second communication cycle is longer than the first communication cycle. For this reason, there is no need to perform processing for continuing to successively transmit the second biological information of a large data amount in a short communication cycle. As a result, it is possible to maintain power saving performance of BLE, or the like while transmitting the second biological information from the biological information measurement apparatus 100 to the information processing apparatus 200.

In order to perform communication at the transmission timing shown in FIG. 3, the communication unit 150 determines the transmission timing of the second biological information based on the time output from the time output unit 170 and transmits the second biological information at the determined transmission timing.

With this, it is possible to perform transmission/reception of data in a required communication cycle, or the like.

In this example, the detection cycle of the first biological information is set to the same interval of one second as the first communication cycle. For this reason, the information processing apparatus 200 can consider the received first biological information as information detected at the received time. Then, since the first communication cycle is sufficiently short, there is no problem even if the received first biological information is considered as information detected at the received time.

Meanwhile, the detection cycle of the second biological information is often a cycle shorter than the second communication cycle. For example, the detection cycle of the second biological information is the same cycle as the detection cycle of the first biological information. For this reason, even if only the second biological information is transmitted in the second communication cycle, the information processing apparatus 200 cannot determine when the received second biological information is detected.

Accordingly, the storage unit 190 of the biological information measurement apparatus 100 stores the second biological information corresponding to the time information (logging or in association with the time information) in association with the measurement time output from the time output unit 170. It should be noted that the measurement time is the time output from the time output unit 170 at the timing when the biological information is detected.

With this, it is possible to allow the information processing apparatus 200 to specify the measurement time of the received second biological information, or the like.

The storage unit 190 may store not only the second biological information but also the first biological information in association with (by logging) the measurement time. Then, for example, after communication between the biological information measurement apparatus 100 and the information processing apparatus 200 is disconnected and reconnected, the communication unit 150 may transmit the non-transmitted first biological information stored in the storage unit 190 during disconnection of communication to the information processing apparatus 200 according to the specific profile. On this occasion, the communication unit 150 may transmit not only the first biological information but also the measurement time stored in association with the first biological information. That is, the second biological information may include the first biological information accumulated in the storage unit 190.

With this, it is possible to collectively transmit the first biological information, which is detected while communication with the information processing apparatus 200 is disconnected, after reconnection, or the like, and it is possible to allow the information processing apparatus 200 to specify the measurement time of the first biological information detected during disconnection of communication, or the like.

As described above, the second biological information measured and recorded by the biological information measurement apparatus 100 is transmitted from the biological information measurement apparatus 100 to the information processing apparatus 200 (smartphone), and is then transmitted from the information processing apparatus 200 to the Web server.

Specifically, as described referring to FIG. 3, the biological information measurement apparatus 100 transmits the second biological information for previous one hour to the information processing apparatus 200 every hour on the hour. Then, the information processing apparatus 200 receives the second biological information from the biological information measurement apparatus 100, and then uploads the second biological information to the Web server.

On this occasion, since all information processing apparatuses 200 which are used in a market perform upload to the Web server at the same timing, load concentration onto the Web server occurs, and there is a risk of the occurrence of significant failure.

Accordingly, in the embodiment, the transmission timing of the second biological information is shifted for each biological information measurement apparatus 100. With this, the information processing apparatuses 200 are prevented from uploading the second biological information to the Web server together with the same timing.

Specifically, the communication unit 150 of the biological information measurement apparatus 100 obtains a delay time of the transmission timing of the biological information based on apparatus-specific information. Then, the communication unit 150 obtains a first transmission timing based on the time output from the time output unit 170 and transmits the biological information (second biological information) at a second transmission timing delayed from the first transmission timing by the obtained delay time.

Then, the communication unit 210 of the information processing apparatus 200 receives the biological information (second biological information) at the second transmission timing.

Here, as the apparatus-specific information, a unique circuit ID which is given for each individual at the time of manufacturing of the biological information measurement apparatus 100 is used. Then, the circuit ID is input to a hash function expressed by Expression (1) to calculate a delay time DT. In Expression (1), IN represents the circuit ID, and DT represents the delay time. In this example, the delay time of 0 to 599 seconds can be generated.

Equation 1

$$DT = IN \bmod 600 \quad (1)$$

Figure 4:
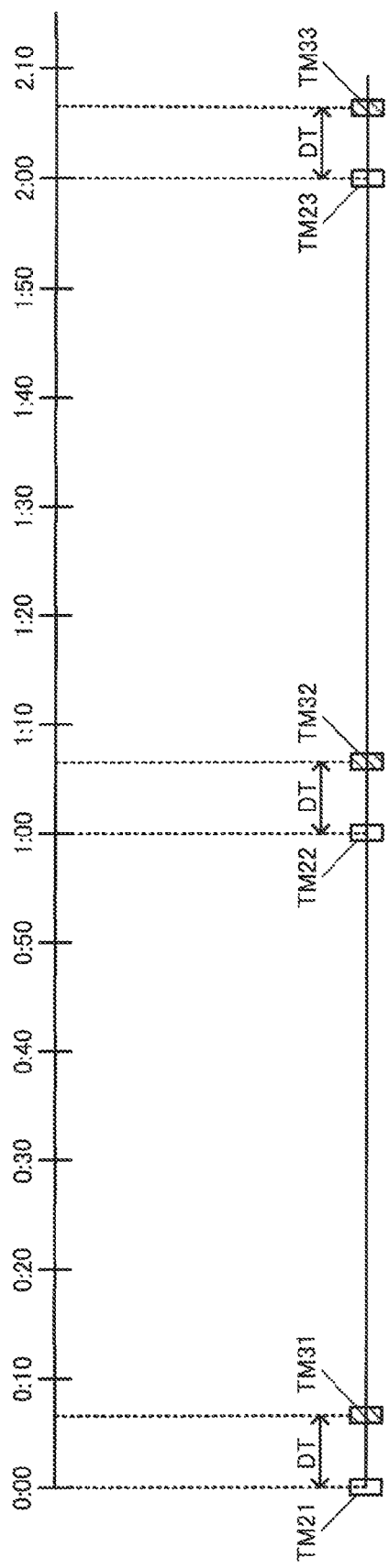
FIG. 4 is an explanatory view of a transmission timing distributed by a delay time.

The first transmission timing is, for example, every hour on the hour, and in FIG. 4, is from the timing TM21 to the timing TM23.

Then, as the second transmission timing, the time delayed from the first transmission timing by the obtained delay time DT is obtained. Specifically, in the example of FIG. 4, the timing TM31 to the timing TM33 become the second transmission timing.

As described above, since the circuit ID (apparatus-specific information) is information which is different for each the biological information measurement apparatuses 100, the delay time DT calculated by the above-described hash function becomes a distributed value.

With this, since the timing of transmission of the second biological information to the information processing apparatus 200 is distributed, it is possible to distribute the timing of transmission of the second biological information from the information processing apparatus 200 to the Web server. Accordingly, it is possible to realize load distribution onto the Web server.

Figure 5:
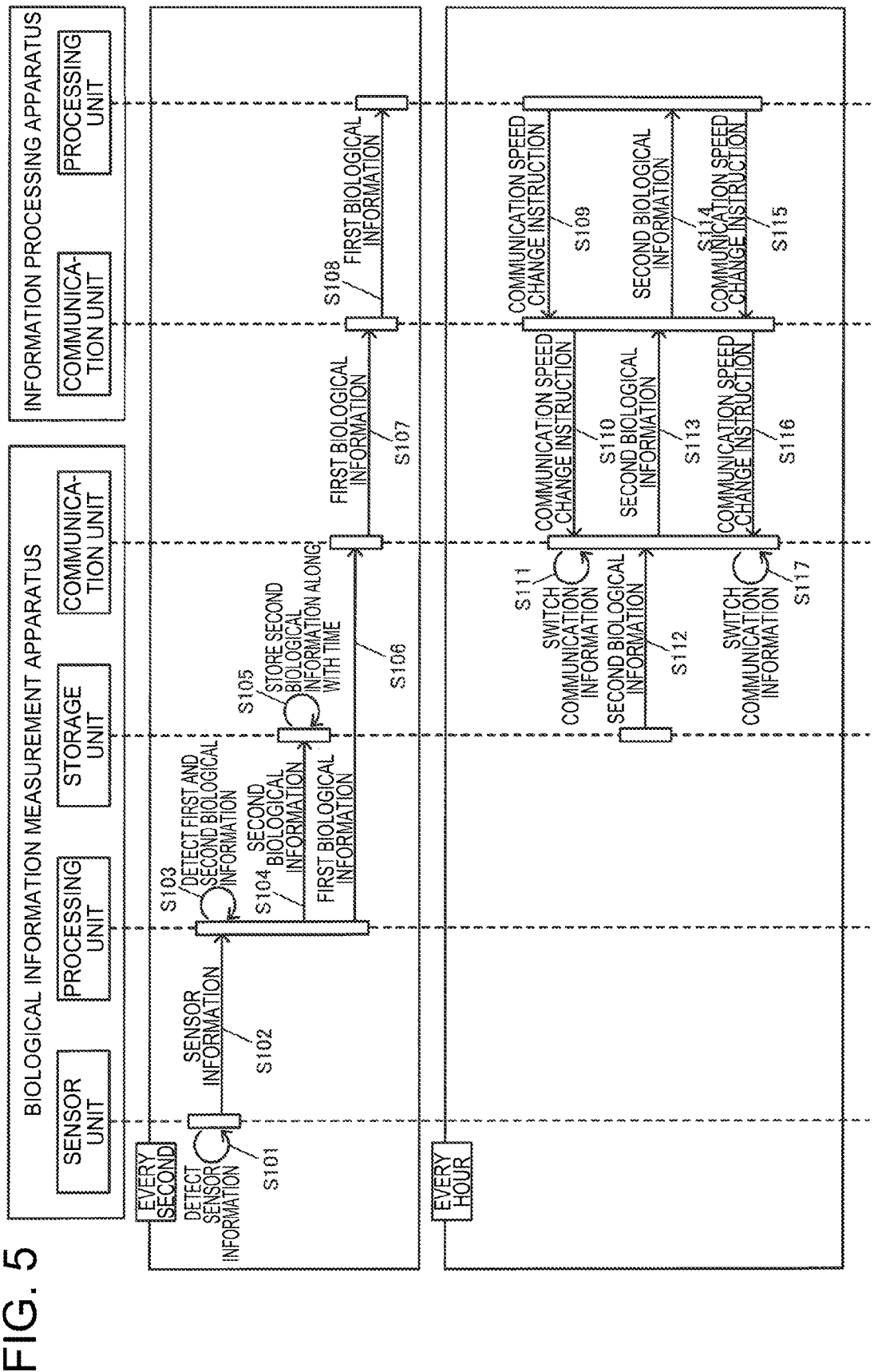
FIG. 5 is a sequence diagram illustrating the flow of entire processing of the embodiment.

Next, the flow of the processing of the embodiment will be described referring to the sequence diagram of FIG. 5.

First, the sensor unit 110 of the biological information measurement apparatus 100 detects sensor information every second (S101), and notifies the sensor information to the processing unit 130 (S102).

Next, the processing unit 130 detects first biological information and second biological information based on sensor information (S103). Then, the storage unit 190 acquires the second biological information from the processing unit 130 (S104), and stores the second biological information in association with the measurement time of the second biological information obtained from the time output unit 170 (S105).

The communication unit 150 acquires the first biological information from the processing unit 130 (S106), and transmits the first biological information to the communication unit 210 of the information processing apparatus 200 according to the standard profile of BLE (S107). Then, the processing unit 230 of the information processing apparatus 200 acquires the first biological information from the communication unit 210 (S108), and performs various kinds of processing. It should be noted that Steps S104 and S105 and Steps S106 to S108 may be reversed or may be performed in parallel. The above is a series of flow of transmission/reception processing of the first biological information. The processing of Steps S101 to S108 is performed in every first communication cycle (first detection cycle).

Next, the processing unit 230 of the information processing apparatus 200 instructs to change a communication speed from a first communication speed to a second communication speed faster than the first communication speed before receiving the second biological information. That is, the processing unit 230 notifies the communication speed change instruction to the second communication speed to the communication unit 210 (S109). Here, the first communication speed is a communication speed at the time of the transmission of the first biological information in Step S107.

Then, the communication unit 210 of the information processing apparatus 200 transmits the communication speed change instruction to the communication unit 150 of the biological information measurement apparatus 100 (S110).

The communication unit 150 of the biological information measurement apparatus 100 changes the communication speed based on the received communication speed change instruction (S111). That is, the communication unit 150 changes the communication speed from the first communication speed to the second communication speed faster than the first communication speed before transmitting the second biological information (S111).

Then, the communication unit 150 acquires the second biological information from the storage unit 190 along with the measurement time (S112). The communication unit 150 transmits the second biological information to the communication unit 210 of the information processing apparatus 200 at the above-described second transmission timing by an upload sequence of a specific profile described below in detail referring to FIG. 9 and the like (S113). Then, the processing unit 230 of the information processing apparatus 200 acquires the second biological information from the communication unit 210 (S114).

Then, the processing unit 230 instructs to change the communication speed to a third communication speed slower than the second communication speed after transmission of the second biological information is completed (S115). That is, the processing unit 230 notifies the communication speed change instruction to the third communication speed to the communication unit 210 (S115). Here, the third communication speed may be the same communication speed as the first communication speed.

Then, the communication unit 210 of the information processing apparatus 200 transmits a communication speed change instruction to the communication unit 150 of the biological information measurement apparatus 100 (S116).

In response to this, the communication unit 150 of the biological information measurement apparatus 100 changes the communication speed based on the received communication speed change instruction (S117). That is, the communication unit 150 changes the communication speed to the third communication speed slower than the second communication speed after transmission of the second biological information is completed (S117). The above is a series of flow of transmission/reception processing of the second biological information. The processing of Steps S109 to S117 is performed in every second communication cycle.

In this way, since the communication speed increases only while communication is performed according to the specific profile, and the communication speed decreases when communication is performed without depending on the specific profile, it is possible to maintain power saving performance, or the like.

When transmitting the biological information according to the specific profile, the following processing is performed.

First, the communication unit 150 of the biological information measurement apparatus 100 transmits a notification that the biological information is transmittable to the information processing apparatus 200 at the second transmission timing when the biological information is transmittable.

Then, when the communication unit 210 receives, from the biological information measurement apparatus 100, a notification that the second biological information is transmittable, the processing unit 230 of the information processing apparatus 200 instructs the biological information measurement apparatus 100 to start transmission of the second biological information. On this occasion, the communication unit 210 transmits the transmission start instruction to the biological information measurement apparatus 100.

Subsequent processing is the same as processing after T101 of FIG. 9 described below in detail. Specifically, when receiving the transmission start instruction from the information processing apparatus 200, the communication unit 150 transmits the upload data size of the biological information to the information processing apparatus 200 with a third characteristic having a property of read with acknowledge and starts transmission of the biological information.

3. Communication Method Based on Specific Profile

Next, the details of a communication method based on the specific profile of the embodiment will be described.

3.1. System Configuration Example

Figure 6A:
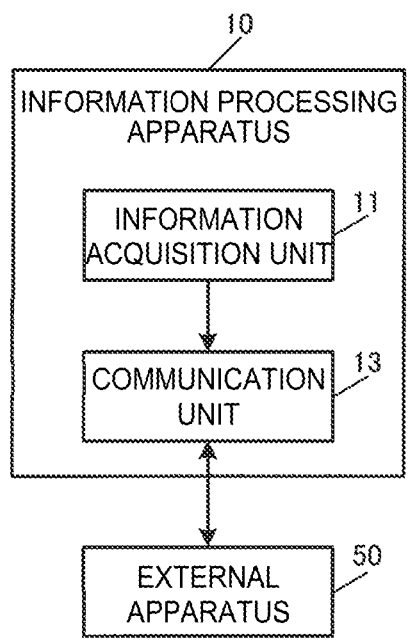
FIGS. 6A and 6B show another system configuration example of the embodiment.

First, FIG. 6A shows a configuration example of an information processing apparatus 10 of the embodiment. The information processing apparatus 10 of the embodiment includes an information acquisition unit 11 which acquires information, and a communication unit 13 which performs communication with an external apparatus 50 through proximity wireless communication. It should be noted that the information processing apparatus 10 corresponds to the biological information measurement apparatus 100 of FIG. 1 described above, and the external apparatus 50 corresponds to the information processing apparatus 200 of FIG. 1 described above. For example, the information processing apparatus 10 of the embodiment is realized by a health care device. Then, the functions of the information acquisition unit 11 and the communication unit 13 can be realized by hardware, such as various processors (CPU and the like) or an ASIC (gate array or the like), a program, or the like. The configuration of the information processing apparatus 10 is not limited to the configuration of FIG. 6A, and various modifications may be made by omitting some components, adding other components, or the like. However, some or all of the functions of the information processing apparatus 10 may be realized by a server connected to the external apparatus 50 through communication.

3.2. Property

In BLE, a property is given for each characteristic. The property determines the type of a series of communication sequence when performing transmission/reception of data using the characteristic, and is roughly classified into write and read.

First, read is a property given to a characteristic when a server (or a host, in this example, a health care device) transmits data to a client (peripheral, in this example, a smart device). Read includes read with acknowledge (ACK) and read with no acknowledge. In other words, according to the above-described specification of https://www.bluetooth.org/ja-jp/specification/adopted-specifications, read with acknowledge is Indicate, and read with no acknowledge is Notification.

Then, when data is transmitted from the server to the client with a characteristic having read with acknowledge, and the client receives data normally, acknowledge is returned from the client to the server with the same characteristic.

When data is transmitted from the server to the client with a characteristic having read with no acknowledge, it is not necessary to return acknowledge from the client to the server regardless of the success/failure of data reception.

Contrary to read, write is a property given to a characteristic when transmitting data from the client to the server.

Similarly to read, write includes write with acknowledge and write with no acknowledge. In other words, according to the above-described specification of https://www.bluetooth.org/ja-jp/specification/adopted-specifications, write with acknowledge is Write With Response or Write With Acknowledge, and write with no acknowledge is Write With No Response or Write With No Acknowledge.

Then, when data is transmitted from the client to the server and the server normally receives data with a characteristic having write with acknowledge, acknowledge is returned from the server to the client with the same characteristic.

When data is transmitted from the client to the server with a characteristic having write with no acknowledge, it is not necessary to return acknowledge from the server to the client regardless of the success/failure of data reception.

3.3. Upload Sequence

Figure 6B:
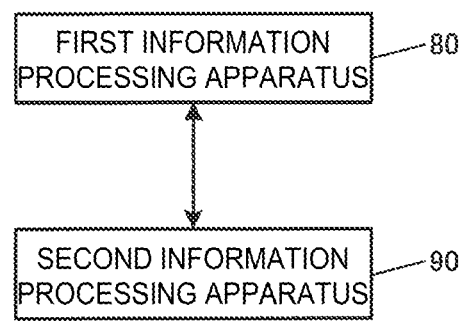

Next, an upload sequence using the specific profile will be described. First, a communication system of this example is shown in FIG. 6B. The communication system of this example includes a first information processing apparatus 80 which acquires information, and an second information processing apparatus 90 which performs communication with the first information processing apparatus 80 through proximity wireless communication. It should be noted that the first information processing apparatus 80 corresponds to the above-described information processing apparatus 10 (server, for example, a health care device, a biological information measurement apparatus, or measurement equipment), and the second information processing apparatus 90 corresponds to the above-described external apparatus 50 (client, for example, a smartphone or other smart devices).

According to the embodiment, in the communication system, a communication unit 13 of the first information processing apparatus 80 divides data of information acquired by an information acquisition unit 11 into a plurality of blocks each having a plurality of packets (performs block division).

Figure 7:
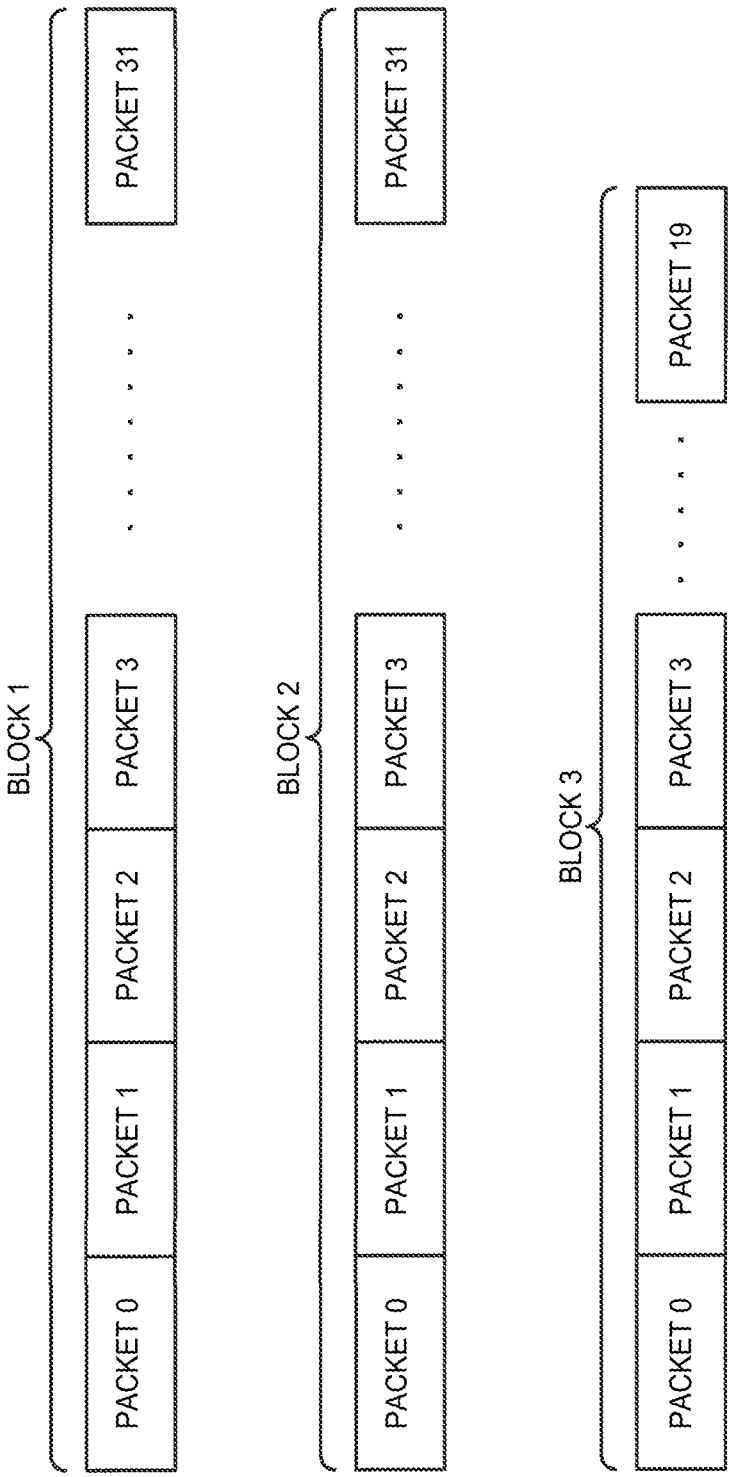
FIG. 7 is an explanatory view of a block.

In the specific profile of the embodiment, a unit, called a block having a plurality of packets, is defined as a unit of data. For example, a specific example of a block having a maximum of 32 packets in one group is shown in FIG. 7. A block 1 and a block 2 shown in FIG. 7 include a packet 0 to a packet 31, and a block 3 includes a packet 0 to a packet 19. In this way, the maximum number of packets included in each block shown in FIG. 7 is 32; however, the number of packets included in each block may be not necessarily the maximum number of packets. It should be noted that, in the following example and sequence diagrams of FIGS. 9 to 12 described below, description will be provided as to a case of transferring the block 1 to the block 3 shown in FIG. 7.

Figure 8:
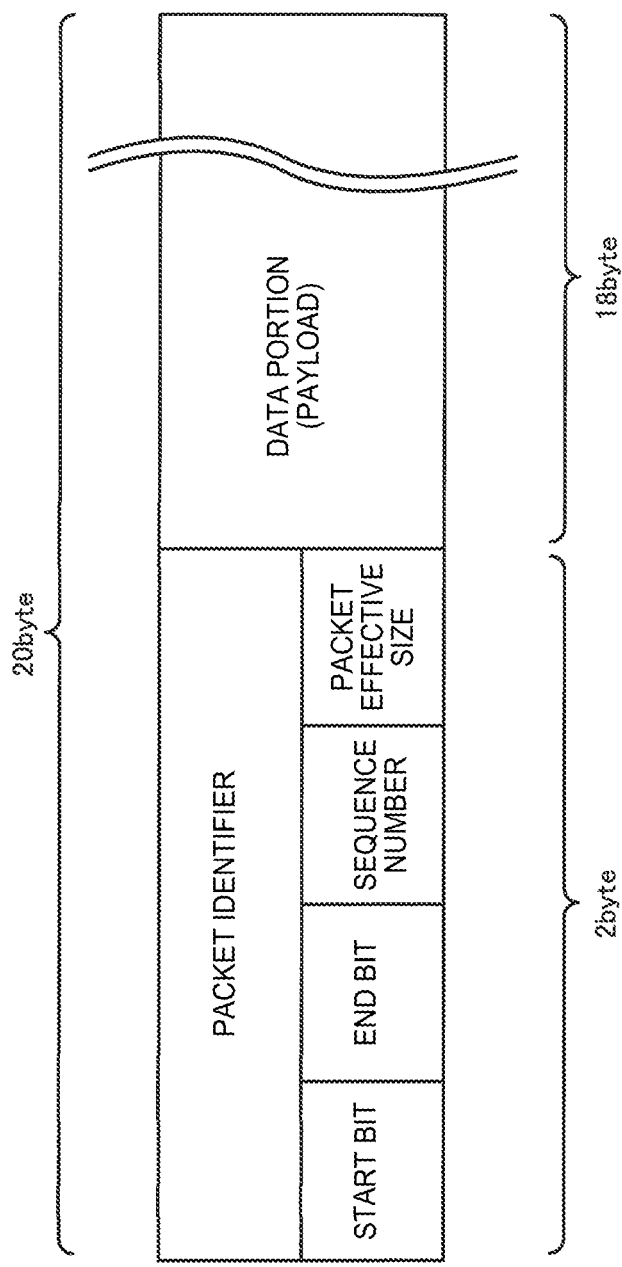
FIG. 8 is an explanatory view of a packet.

As a packet, a packet shown in FIG. 8 is used. Specifically, a packet has a 2-byte packet identifier and an 18-byte data portion (payload). In the data portion, data of information acquired by the information acquisition unit 11 is divided and stored. Then, the packet identifier includes a start bit, an end bit, a sequence number, and a packet effective size.

First, the start bit is a bit which is set to 1 for a first packet of the entire data to be transmitted and is set to 0 for other packets. For example, in the example of FIG. 7, the start bit of the packet 0 included in the block 1 becomes 1, and the start bits of all other packets become 0.

Next, the end bit is a bit which is set to 1 for the last packet of the entire data to be transmitted and is set to 0 for other packets. For example, in the example of the FIG. 7, the end bit of the packet 19 included in the block 3 becomes 1, and the end bits of all other packets become 0.

Then, the sequence number is a number which is the order of the packets included in each block. For example, the sequence number of the packet 0 included in the block 0 becomes 0, and the sequence number of the packet 1 included in the block 0 becomes 1. In this example, since the sequence number is allocated by a serial number for each block, the sequence number of the packet 0 included in the block 1 and the sequence number of the packet 0 included in the block 2 become 0.

The packet effective size is the size of effective data included in the data portion. In this example, since the data portion is 18 bytes, the maximum packet effective size is 18 bytes; however, the packet effective size to be set is not necessarily the maximum value. For example, when the packet effective size is less than 18 bytes, all of the remaining bits are 0, and the entire size of the packet is arranged to 20 bytes.

Then, in the embodiment, the communication unit 13 transmits a plurality of blocks to the second information processing apparatus 90 in units of blocks, and on this occasion, a plurality of packets included in each block are successively transmitted.

On this occasion, when acknowledge is transmitted to the first information processing apparatus 80 each time the second information processing apparatus 90 receives each packet, the first information processing apparatus 80 waits for a response each time transmitting a packet. For this reason, a lot of time is required until transmission of the entire data is completed. This means deterioration of communication speed.

Accordingly, in this embodiment, the communication unit 13 (the above-described communication unit 150) transmits a plurality of blocks with a first characteristic having a property of read with no acknowledge, for example, in units of blocks. That is, the communication unit 13 successively transmits the packet 0 to the packet 31 of the block 1 with the first characteristic without waiting for a response from the second information processing apparatus 90.

In response to this, the second information processing apparatus 90 receives (each block of) a plurality of blocks with the first characteristic and transmits the reception result of (each of) the blocks to the first information processing apparatus 80 with a second characteristic having a property of write with acknowledge. That is, the second information processing apparatus 90 transmits the reception result (acknowledge) for each block, instead of transmitting acknowledge for each packet.

Then, the communication unit 13 of the first information processing apparatus 80 receives the reception result of (each of) the blocks in the external apparatus 50 (second information processing apparatus 90 or the above-described information processing apparatus 200) with the second characteristic.

When acknowledge to transmission of (each of) the blocks is received with the second characteristic as the reception result, the communication unit 13 determines that reception of (each of) the blocks by the external apparatus 50 (second information processing apparatus 90) is successful. Since the second characteristic has the property of write with acknowledge, the communication unit 13 subsequently further returns acknowledge representing normal reception as the reception result of the block with the second characteristic.

As described above, the first information processing apparatus 80 transmits information to the second information processing apparatus 90 in units of blocks, and the first information processing apparatus 80 receives the reception result from the second information processing apparatus 90 in units of blocks. That is, the first information processing apparatus 80 only receives a single reception result, whereby it is possible to determine the success/failure of transmission of a plurality of packets. For this reason, it is possible to reduce the response waiting time, thereby reducing the transfer time of each block.

As described above, since the sequence number is allocated to each packet, data stored in the data portion of each packet after reception is connected in order of sequence number, thereby restoring original data.

Accordingly, it is possible to transmit/receive data of the second data amount greater than the first data amount, which is transmittable/receivable by the standard profile of proximity wireless communication, through proximity wireless communication.

Next, the flow of specific processing of the upload sequence will be described referring to the sequence diagram of FIG. 9. In the specific example of FIG. 9, the block 1 to the block 3 of FIG. 7 are transmitted from measurement equipment (first information processing apparatus 80) to a smartphone (second information processing apparatus 90).

First, when information is transmittable, the communication unit 13 transmits the upload data size of information to the external apparatus 50 with the third characteristic having read with acknowledge (Indicate) (T101).

Specifically, a characteristic named Upload Data Size is used as the third characteristic, and the condition that the data size of the block 1 is 640 Bytes, the data size of the block 2 is 640 Bytes, and the data size of the block 3 is 400 Bytes is transmitted from the measurement equipment to the smartphone (T101).

Then, when the upload data size could be normally received, the communication unit of the smartphone transmits acknowledge to the measurement equipment with a characteristic of the same Upload Data Size (T102).

With this, it is possible to give a notification about the start of transmission of data and the upload data size, and to receive that the external apparatus 50 understands the start of transmission, or the like.

Next, as described above, the communication unit 13 of the measurement equipment transmits the block 1 with a first characteristic named Upload Data (T103). Since Upload Data has a property of read with no acknowledge (Notification), as described above, it is not necessary to transmit acknowledge each time the smartphone receives a packet from the measurement equipment side.

For this reason, the communication unit of the smartphone transmits acknowledge (the reception result of the block 1) representing normal reception of the block 1 with a second characteristic named Upload Order after reception of the block 1 (T104). It should be noted that this example is a case where all of the packet 0 to the packet 31 included in the block 1 could be normally received. Since Upload Order has a property of write with acknowledge (Write With Response), when the reception result could be normally received, the communication unit 13 of the measurement equipment further returns acknowledge (T105).

Next, in regard to transmission/reception of the block 2, similarly, the communication unit 13 of the measurement equipment transmits the block 2 with Upload Data (T106). Then, the communication unit of the smartphone transmits the reception result with the characteristic of Upload Order (T107), and in response to this, the measurement equipment returns acknowledge (T108). The same applies to transmission/reception of the block 3 (T109 to T111).

Figure 9:
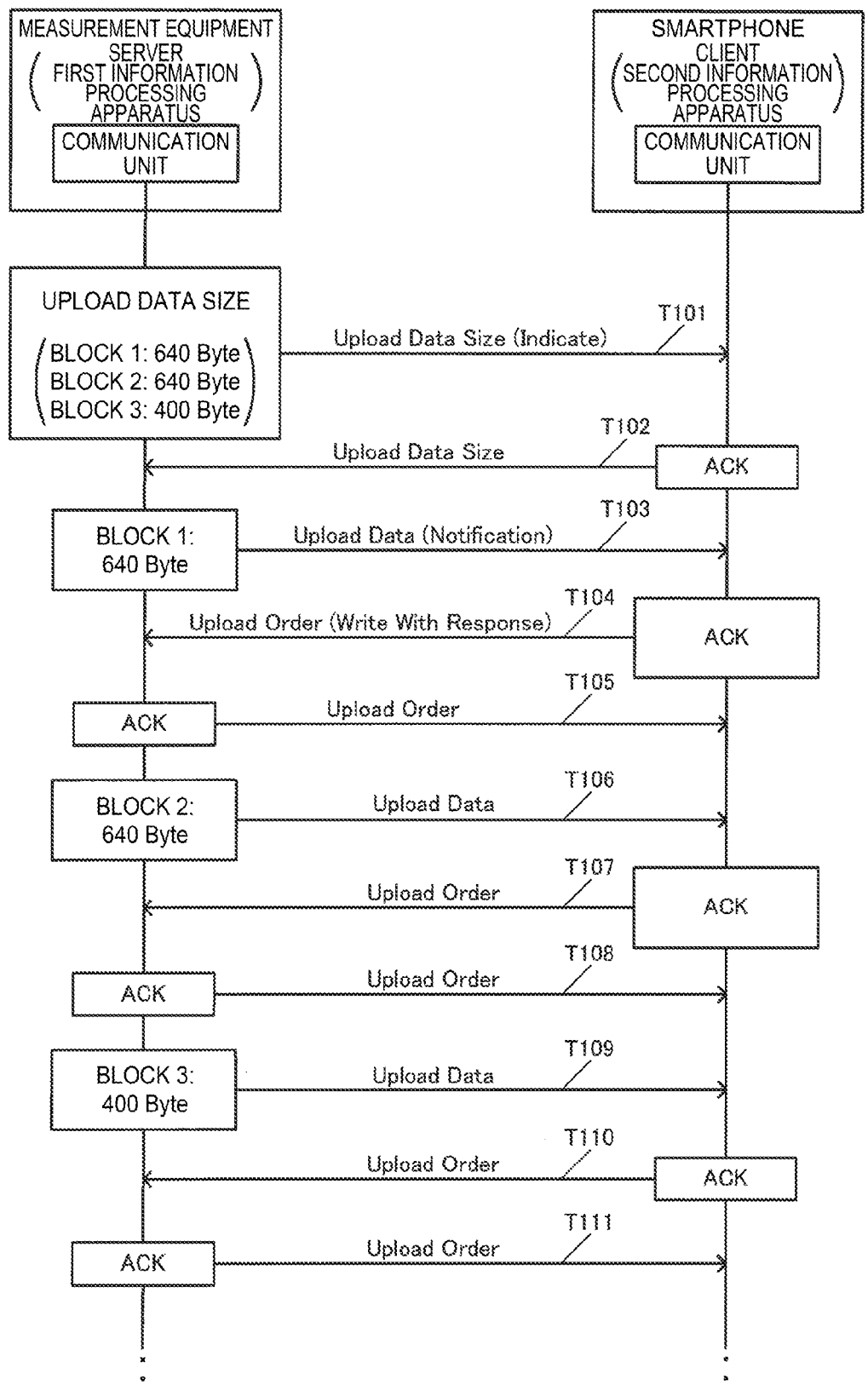
FIG. 9 is a sequence diagram illustrating the flow of processing of an upload sequence.
Figure 10:
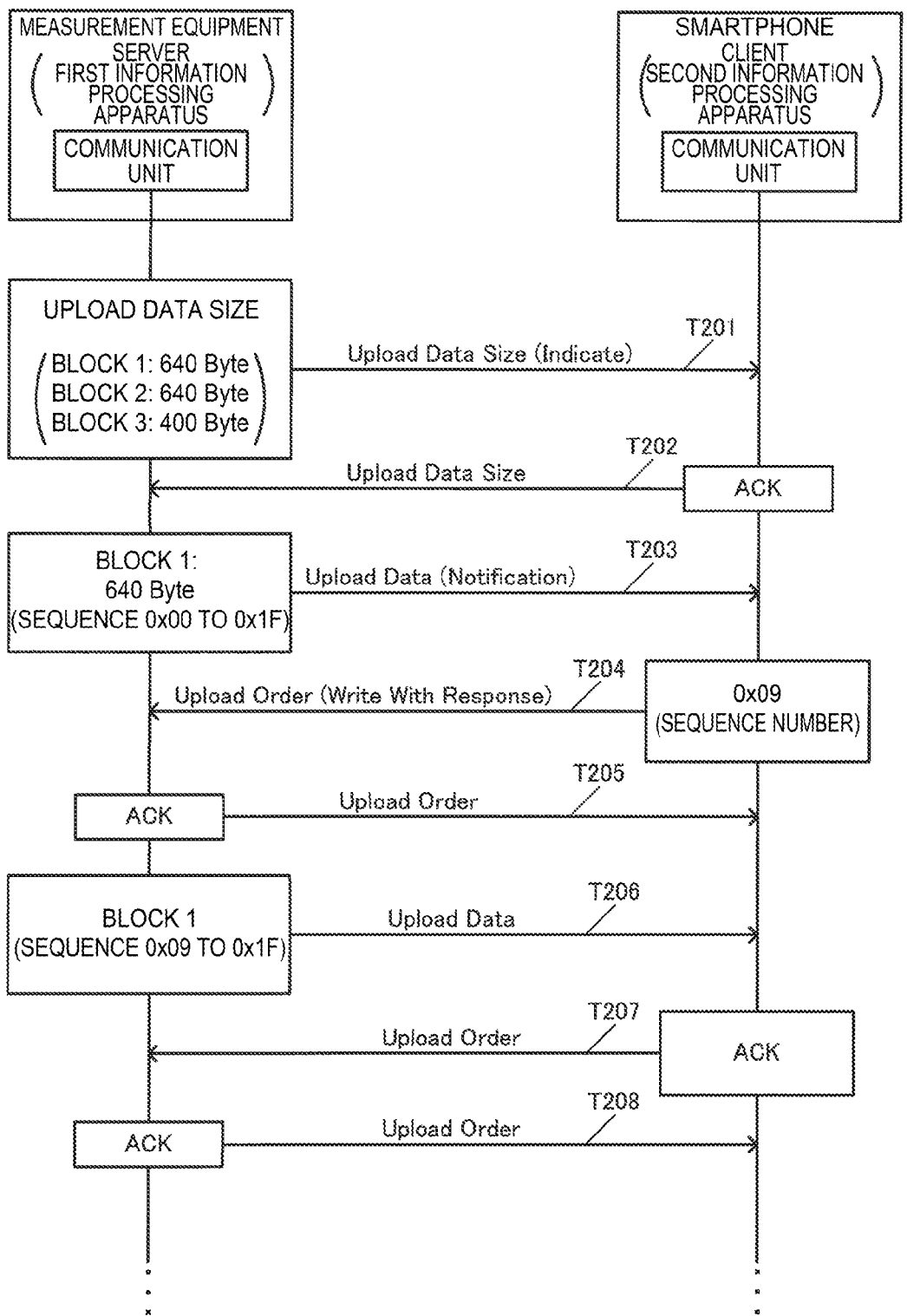
FIG. 10 is another sequence diagram illustrating the flow of processing of an upload sequence.

In the example of FIG. 9 described above, although each of the block 1 to the block 3 could be normally received by single transmission, there may be a case where each block cannot be normally received. On this occasion, retransmission of the block is performed. In this case, the flow of processing is shown in the sequence diagram of FIG. 10. It should be noted that T201 to T203 are the same as T101 to T103 of FIG. 9, thus, description thereof will not be repeated.

In this example, it is assumed that, in T203, the communication unit 13 of the measurement equipment transmits the packet 0 of the sequence number 0x00 to the packet 31 of the sequence number 0x1F included in the block 1, and as a result, the smartphone fails in reception of the packet 9 of the sequence number 0x09.

In this case, the communication unit of the smartphone transmits the sequence number (in this case, 0x09) of the first packet failed in reception to the measurement equipment with the characteristic of Upload Order described above (T204). Meanwhile, when the sequence number could be normally received, the communication unit 13 of the measurement equipment returns acknowledge (T205).

Then, when a sequence number representing one of a plurality of packets included in (each of) the transmitted blocks is received with the second characteristic (Upload Order) as the reception result of (each of) the blocks, the communication unit 13 performs retransmission from the packet corresponding to the sequence number among a plurality of packets (T206).

That is, in this example, since the sequence number 0x09 is received, the communication unit 13 retransmits the packets after the sequence number 0x09, that is, the packet 9 of the sequence number 0x09 to the packet 31 of the sequence number 0x1F with the characteristic of Upload Data (T206).

With this, it is possible to transmit only the packets after packet reception fails, or the like, instead of retransmitting all of a plurality of packets included in each block.

It should be noted that, in this example, for example, even if the smartphone could normally receive the packets after the sequence number 0x0A, all of the packets after the sequence number 0x09 are retransmitted. With this, it is possible to suppress the data amount to be transmitted from the smartphone to the measurement equipment when retransmission is requested.

Then, when the block 1 is retransmitted and the communication unit of the smartphone could normally receive all of the retransmitted packets, the reception result is transmitted to the measurement equipment with the characteristic of Upload Order (T207), and the communication unit 13 of the measurement equipment returns acknowledge (T208). The flow of subsequent processing is the same as the flow of processing after T106 of FIG. 9.

3.4. Download Sequence

Next, a download sequence using the specific profile will be described. First, a communication system of this example is shown in FIG. 6B. The communication system of this example includes a first information processing apparatus 80 which acquires information, and a second information processing apparatus 90 which performs communication with the first information processing apparatus 80 through the proximity wireless communication. It should be noted that the first information processing apparatus 80 corresponds to the above-described external apparatus 50 (client, for example, a smartphone or other smart devices), and the second information processing apparatus 90 corresponds to the above-described information processing apparatus 10 (server, for example, a health care device, biological information measurement apparatus, or a measurement equipment).

In this way, in the download sequence, the roles of the server and the client are reversed compared to the above-described upload sequence. However, the download sequence is the same as the upload sequence in that data is collectively transmitted in units of blocks and the reception result in units of blocks is returned once. For this reason, description of overlapping portions will be appropriately omitted. It should be noted that a first characteristic to a third characteristic used hereinafter are characteristics different from those described in the upload sequence.

Specifically, in the download sequence of the embodiment, the first information processing apparatus (smartphone) divides data of information to be transmitted into a plurality of blocks each having a plurality of packets as in FIG. 7 described above. Next, the first information processing apparatus transmits a plurality of blocks to the second information processing apparatus (measurement equipment) with a first characteristic having a property of write with no acknowledge, for example, in units of blocks.

Then, the communication unit 13 of the second information processing apparatus receives a plurality of blocks with the first characteristic in units of blocks. The communication unit 13 transmits the reception result of each block to the first information processing apparatus with a second characteristic having a property of read with acknowledge, and the first information processing apparatus receives the reception result with the second characteristic.

With this, similarly to the upload sequence, since it is not necessary to return acknowledge sequentially each time the second information processing apparatus receives each packet, it is possible to reduce the time until transmission of each block is completed.

Since the sequence number is allocated to each packet of each block, it is possible to transmit/receive data of the second data amount greater than the first data amount, which is transmittable/receivable by the standard profile of proximity wireless communication, through proximity wireless communication by the same principle as the upload sequence.

Figure 11:
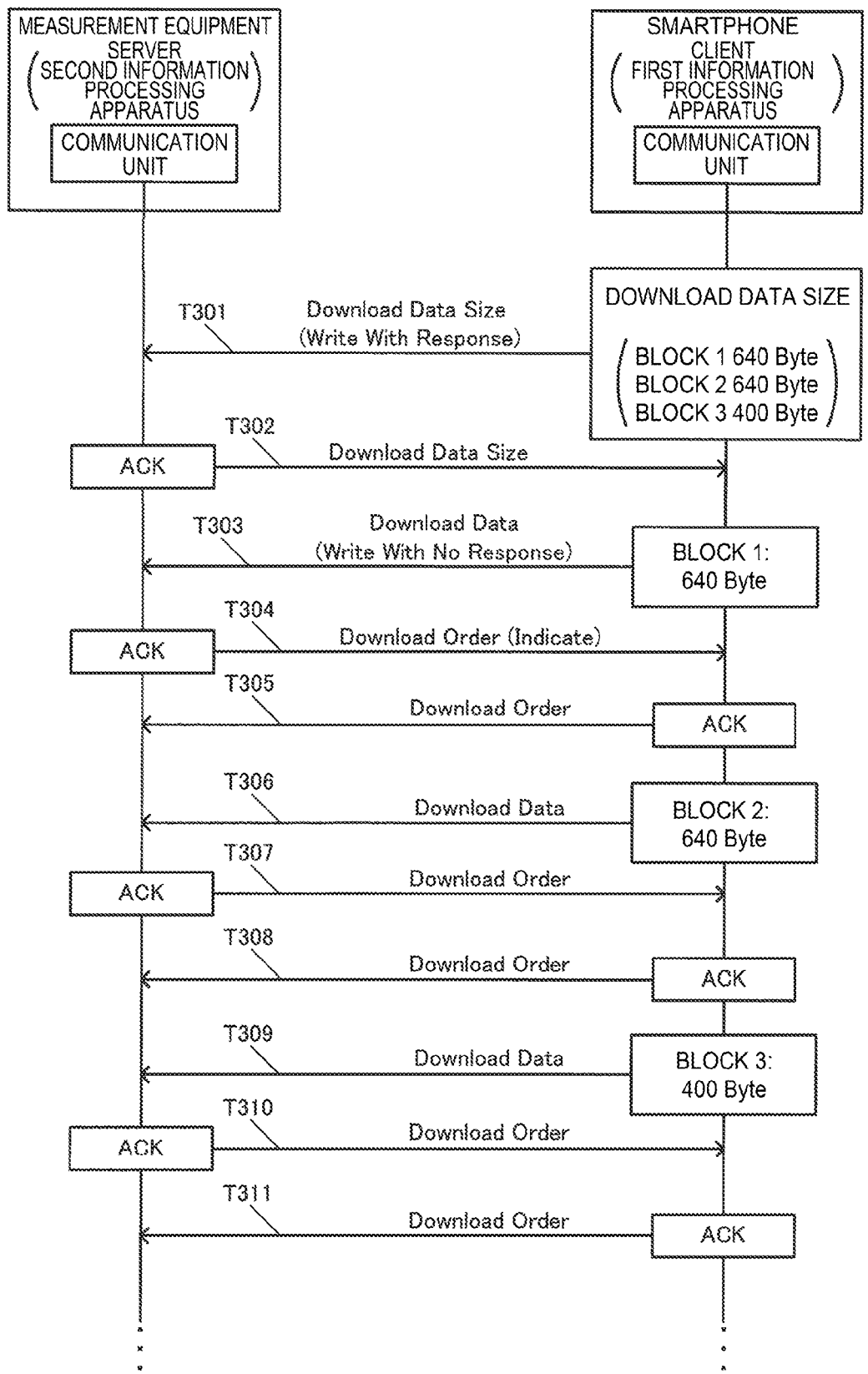
FIG. 11 is a sequence diagram illustrating the flow of processing of a download sequence.
Figure 12:
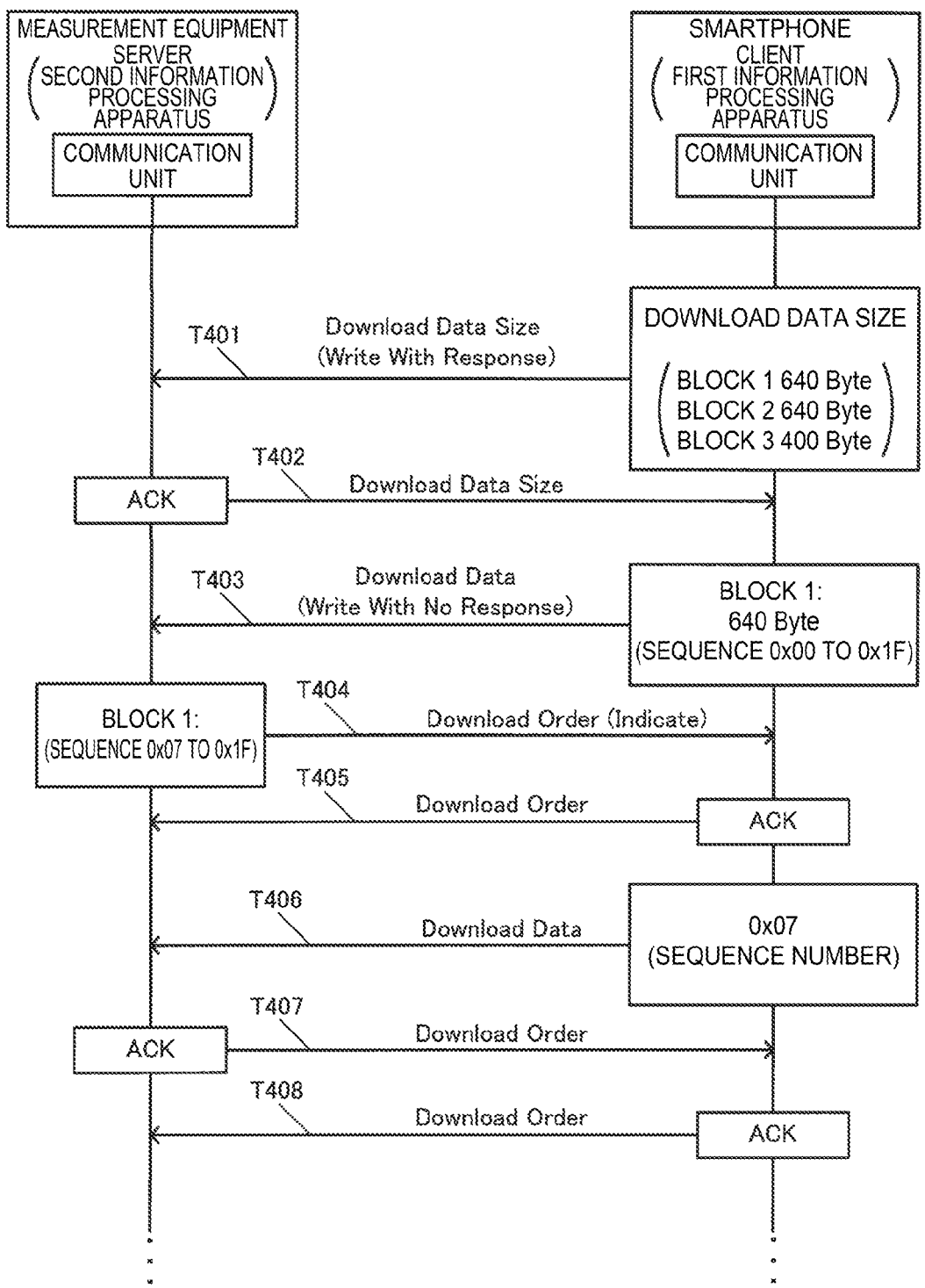
FIG. 12 is another sequence diagram illustrating the flow of processing of a download sequence.

Next, the flow of specific processing of the upload sequence will be described referring to the sequence diagram of FIG. 11. In a specific example of FIG. 11, the block 1 to the block 3 of FIG. 7 are transmitted from the smartphone (first information processing apparatus 80) to the measurement equipment (second information processing apparatus 90).

First, when information is transmittable, the communication unit of the smartphone transmits the download data size of information to the measurement equipment with a third characteristic having a property of write with acknowledge (Write With Response) (T301).

Specifically, a characteristic named Download Data Size is used as the third characteristic, and the condition that the data size of the block 1 is 640 Bytes, the data size of the block 2 is 640 Bytes, and the data size of the block 3 is 400 Bytes is transmitted from the smartphone to the measurement equipment (T301).

Then, when the download data size could be normally received, the communication unit 13 of the measurement equipment transmits acknowledge to the smartphone with the characteristic of the same Download Data Size (T302).

With this, it is possible to allow the measurement equipment to receive the start of transmission of data and the download data size, and to notify the smartphone that the measurement equipment understands the start of transmission, or the like.

Next, as described above, the communication unit of the smartphone transmits the block 1 with a first characteristic named Download Data (T303). Since Download Data has a property of write with no acknowledge (Write With No Response), as described above, it is not necessary to transmit acknowledge each time the measurement equipment receives a packet from the smartphone.

For this reason, the communication unit 13 of the measurement equipment transmits acknowledge (the reception result of the block 1) representing normal reception of the block 1 with a second characteristic named Download Order after reception of the block 1 (T304). It should be noted that this example is a case where all of the packet 0 to the packet 31 included in the block 1 could be normally received. Since Download Order has a property of read with no acknowledge (Indicate), when the reception result could be normally received, the communication unit of the smartphone returns acknowledge with the characteristic of Download Order (T305).

Next, in regard to transmission/reception of the block 2, similarly, the communication unit of the smartphone transmits the block 2 with the characteristic of Download Data (T306). Then, the communication unit 13 of the measurement equipment transmits the reception result with the characteristic of Download Order (T307), and in response to this, the smartphone returns acknowledge (T308). The same applies to transmission/reception of the block 3 (T309 to T311).

Similarly to the upload sequence, in the download sequence, there is a case where the communication unit 13 of the measurement equipment cannot normally receive each block and the smartphone performs retransmission of the block. In this case, the flow of processing is shown in the sequence diagram of FIG. 12. It should be noted that T401 to T403 are the same as T301 to T303 of FIG. 11, thus, description thereof will not be repeated.

In this example, it is assumed that, in T403, the communication unit of the smartphone transmits the packet 0 of the sequence number 0x00 to the packet 31 of the sequence number 0x1F included in the block 1, and as a result, the communication unit 13 of the measurement equipment fails in reception of the packet 7 of the sequence number 0x07.

In this case, the communication unit 13 of the measurement equipment transmits a sequence number corresponding to a packet failed in reception among a plurality of packets included in (each of) the transmitted blocks with the second characteristic as the reception result (T404). Specifically, the communication unit 13 of the measurement equipment transmits the sequence number (in this case, 0x07) of the first packet failed in reception to the smartphone with the characteristic of Download Order described above (T404).

With this, it is possible to notify the sequence number of the first packet failed in reception to the smartphone (external apparatus 50), or the like.

In response to this, when the sequence number could be normally received, the communication unit of the smartphone returns acknowledge (T405).

Next, the communication unit of the smartphone performs retransmission from the packet corresponding to the received sequence number among a plurality of packets (T406). Specifically, in this example, since the sequence number 0x07 is received, the communication unit of the smartphone retransmits the packets after the sequence number 0x07, that is, the packet 7 of the sequence number 0x07 to the packet 31 of the sequence number 0x1F with the characteristic of Download Data (T406).

In response to this, when a sequence number representing one of a plurality of packets included in (each of) of the received bocks is transmitted with the second characteristic as the reception result (T404), the communication unit 13 of the measurement equipment receives a plurality of packets from the packet corresponding to the sequence number again (T406).

With this, it is possible to receive only the packets after failure in reception of the packets again, or the like, instead of receiving all of a plurality of packets included in each block again. It should be noted that, in this example, similarly to the upload sequence, for example, even if the measurement equipment could normally receive the packets after the sequence number 0x08, all of the packets after the sequence number 0x07 are received again.

Then, when the block 1 is received again and the communication unit 13 of the measurement equipment could normally receive all of the retransmitted packets, the reception result is transmitted to the measurement equipment with the characteristic of Download Order (T407), and the communication unit of the smartphone returns acknowledge (T408). The flow of subsequent processing is the same as the flow of processing after T306 of FIG. 11.

If proximity wireless communication is performed between the health care device and the smartphone according to the download sequence described above, it is possible to update firmware of the health care device through the smartphone, or the like.

3.5. Communication Speed Change Sequence

Figure 13:
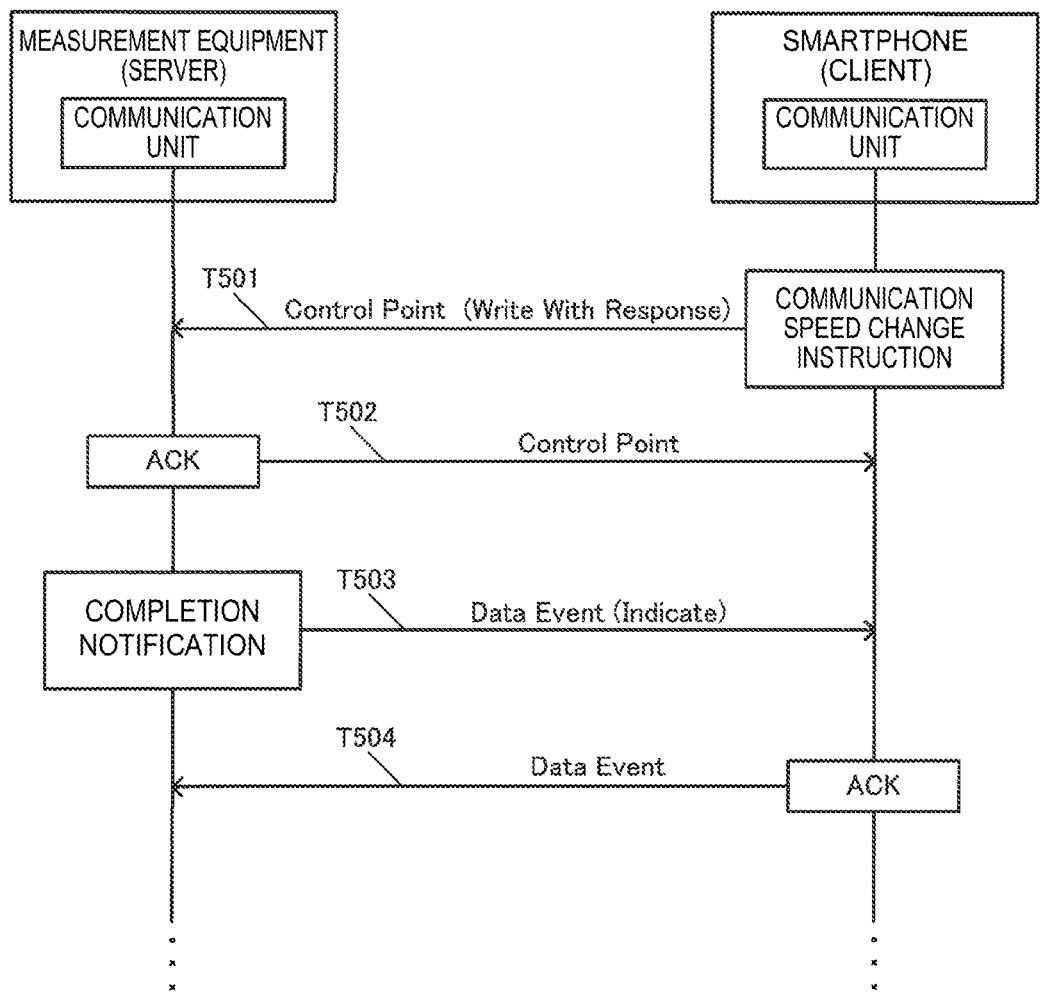
FIG. 13 is a sequence diagram illustrating the flow of processing of a communication speed change sequence.

Next, a communication speed change sequence will be described referring to a sequence diagram of FIG. 13. The communication speed change sequence is performed in the same sequence for both upload and download.

First, the communication unit of the smartphone transmits a communication speed change instruction to the measurement equipment with a fourth characteristic having a property of write with acknowledge (T501). In this example, a characteristic named Control Point is used as the fourth characteristic.

The communication speed change instruction may be information representing a communication speed after change, mode switching information for use in switching between, for example, a low-speed mode and a high-speed mode set in advance, or the like. It should be noted that, when the mode switching information is used as the communication speed change instruction, a communication speed in the low-speed mode and a communication speed in the high-speed mode are set in advance.

In response to this, the communication unit 13 of the measurement equipment receives the communication speed change instruction with the fourth characteristic (Control Point) having the property of write with acknowledge (T501), and returns acknowledge representing normal reception of the communication speed change instruction with Control Point (T502).

Then, the communication unit 13 changes the communication speed based on the received communication speed change instruction and transmits a communication speed change completion notification with a fifth characteristic having a property of read with acknowledge (Indicate) (T503). In this example, a characteristic named Data Event is used as the fifth characteristic.

Finally, when the communication speed change completion notification could be normally received, the communication unit of the smartphone returns acknowledge representing normal reception of the communication speed change completion notification with Data Event (T504), and ends the processing.

With this, it is possible to perform communication at the communication speed represented by the received communication speed change instruction, or the like.

4. Configuration Example of Biological Information Measurement Apparatus

Figure 14A:
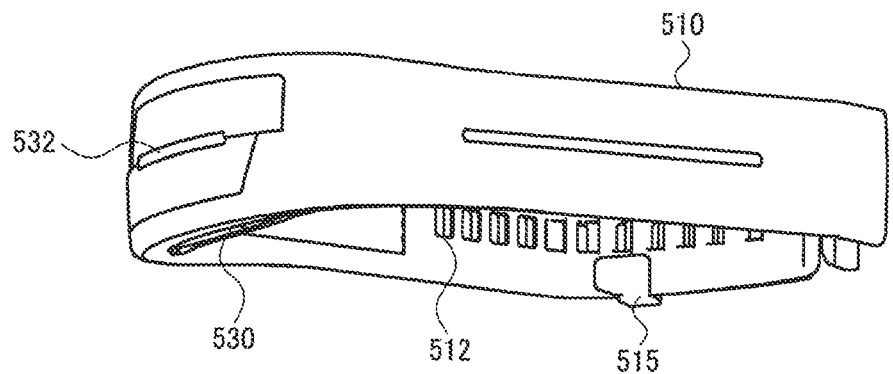
FIGS. 14A and 14B are appearance diagrams of the biological information measurement apparatus of the embodiment.
Figure 14B:
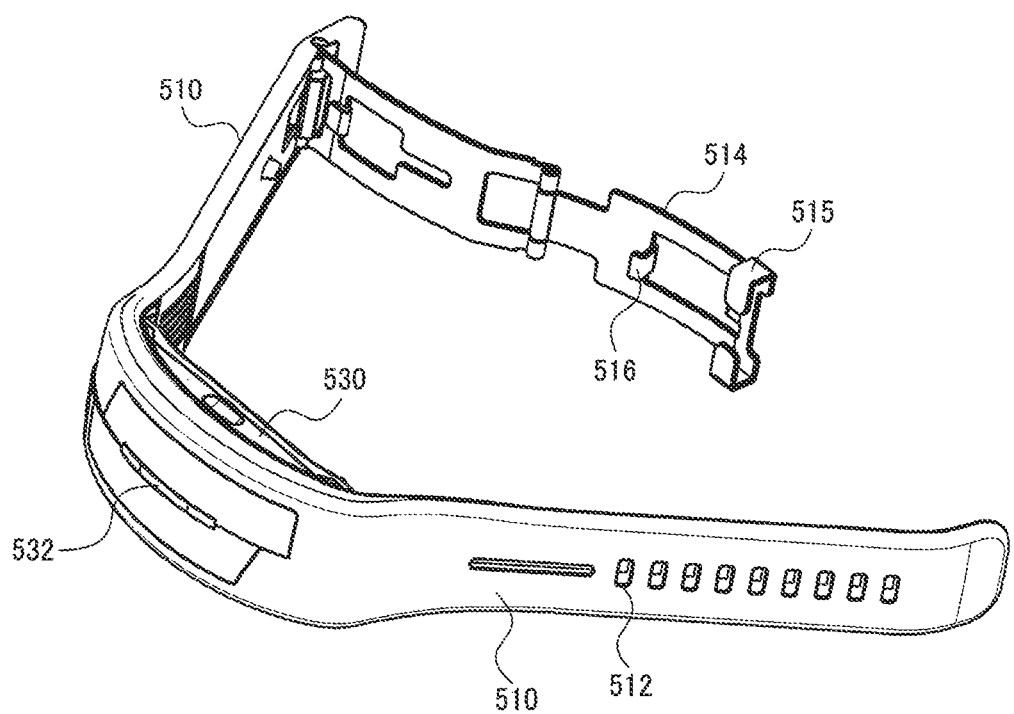
Figure 15:
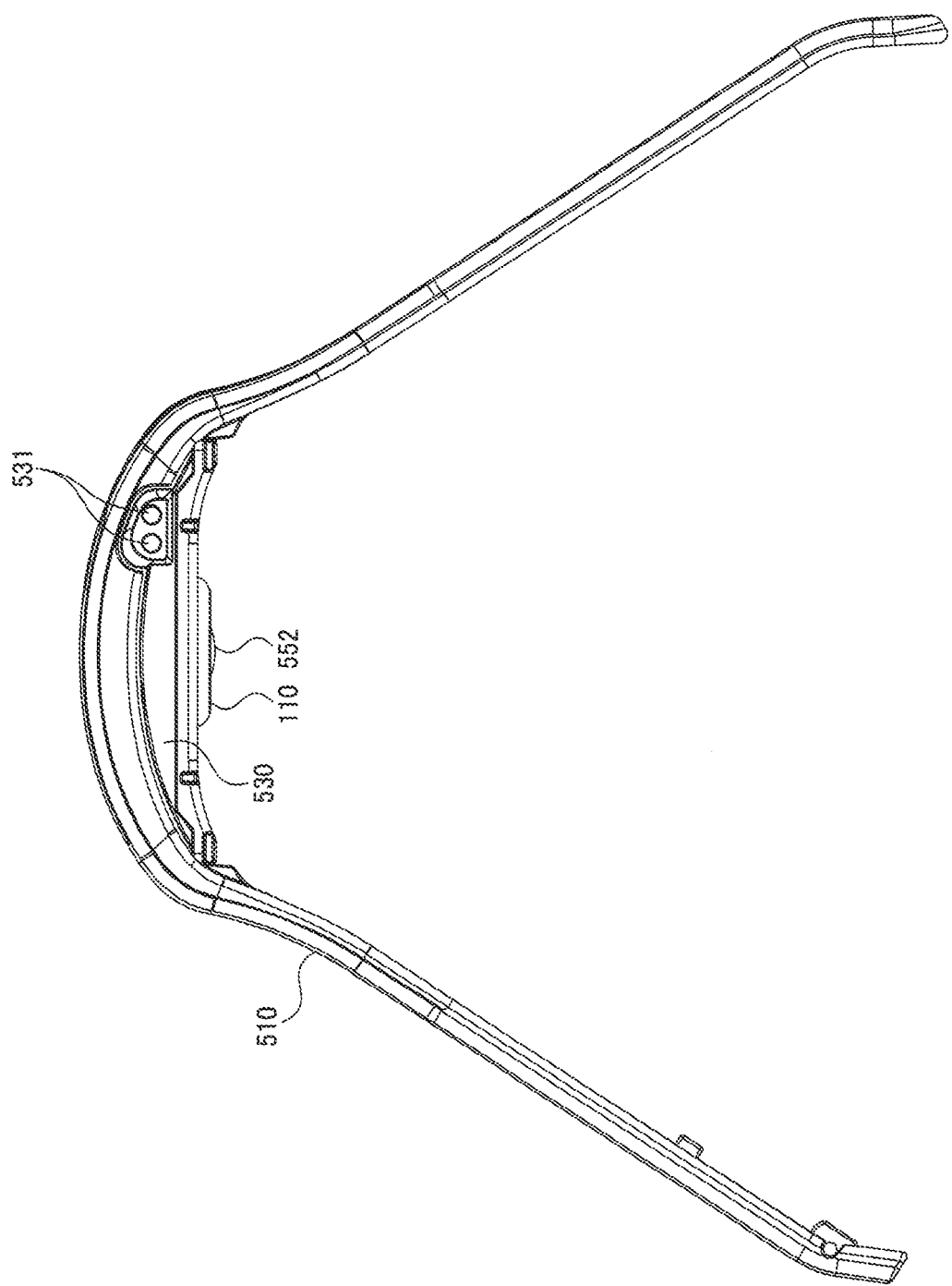
FIG. 15 is an appearance diagram of the biological information measurement apparatus of the embodiment.

FIGS. 14A, 14B, and 15 are appearance diagrams of the biological information measurement apparatus (biological information detection apparatus) of the embodiment. FIG. 14A is a diagram showing the biological information measurement apparatus when viewed from a forward direction, FIG. 14B is a diagram when viewed from an upward direction, and FIG. 15 is a diagram when viewed from a sideward direction.

As shown in FIGS. 14A to 15, the biological information measurement apparatus of the embodiment has a band 510, a case 530, and a sensor unit 110. The case 530 is attached to the band 510. The sensor unit 110 is provided in the case 530. As shown in FIG. 1 described above, the biological information measurement apparatus has the processing unit 130, the communication unit 150, the time output unit 170, and the storage unit 190, and these are provided in the case 530. It should be noted that the biological information measurement apparatus of the embodiment is not limited to the configuration of FIGS. 14A to 15, and the like, and various modifications may be made by omitting some components, replacing some components with other components, adding other components, or the like.

The band 510 is worn around the wrist of the user to mount the biological information measurement apparatus. The band 510 has holes 512 and a buckle 514. The buckle 514 has a band insertion portion 515 and a protrusion 516. The user inserts one end of the band 510 into the band insertion portion 515 of the buckle 514 and inserts the protrusion 516 of the buckle 514 into one of the holes 512 of the band 510, thereby mounting the biological information measurement apparatus on the wrist. In this case, the magnitude of a pressing force against the sensor unit 110 (a pressing force against the surface of the wrist) is adjusted according to the position of the hole 512 into which the protrusion 516 is inserted.

The case 530 corresponds to the main body of the biological information measurement apparatus. Inside the case 530, various components of the biological information measurement apparatus, such as the sensor unit 110 and the processing unit 130, are provided. That is, the case 530 is a housing which stores these components.

The case 530 is provided with a light emitting window 532. The light emitting window 532 is formed of a light transmitting member. Then, the case 530 is provided with a light emitting unit (LED) mounted on a flexible substrate, and light from the light emitting unit is irradiated onto the outside of the case 530 through the light emitting window 532.

As shown in FIG. 15, the case 530 is provided with a terminal portion 531. If the biological information measurement apparatus is mounted on a cradle (not shown), and a terminal portion of the cradle and the terminal portion 531 of the case 530 are electrically connected together. With this, it is possible to charge a secondary battery (battery) provided in the case 530.

The sensor unit 110 detects biological information, such as the pulse wave of a subject. For example, the sensor unit 110 has a light receiving unit and a light emitting unit. The sensor unit 110 has a convex portion 552 which is formed of a light transmitting member and comes into contact with the skin surface of the subject to apply a pressing force to the skin surface. In this way, in a state in which the convex portion 552 applies the pressing force to the skin surface, the light emitting unit emits light, the light receiving unit receives light reflected by the subject (blood vessel), and the light receiving result is output to the processing unit 130 as a detection signal. Then, the processing unit 130 detects biological information, such as a pulse wave, based on the detection signal from the sensor unit 110. It should be noted that the biological information to be detected by the biological information measurement apparatus of the embodiment is not limited to the pulse wave (pulse rate), and the biological information measurement apparatus may be an apparatus which detects biological information (for example, oxygen saturation in blood, body temperature, heartbeat, or the like) other than the pulse wave.

Figure 16:
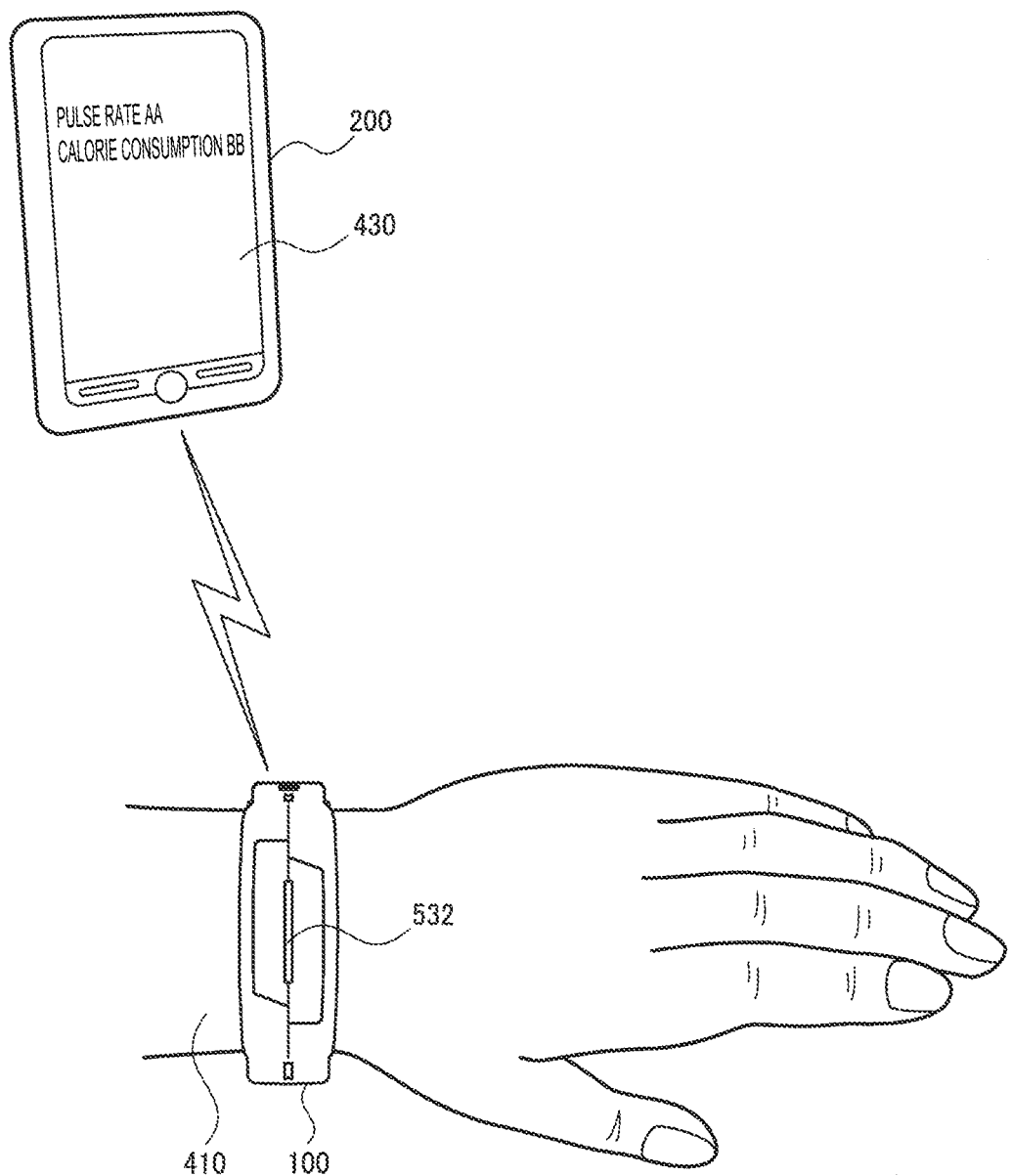
FIG. 16 is an explanatory view for mounting of the biological information measurement apparatus and communication with an information processing apparatus.

FIG. 16 is an explanatory view of mounting of the biological information measurement apparatus 100 and communication with a mobile communication terminal 200.

As shown in FIG. 16, the user who is a subject mounts the biological information measurement apparatus 100 on the wrist 410 like a timepiece. As shown in FIG. 15, the sensor unit 110 is provided on the subject-side surface of the case 530. Accordingly, if the biological information measurement apparatus 100 is mounted, the convex portion 552 of the sensor unit 110 comes into contact with the skin surface of the wrist 410 to apply the pressing force to the skin surface. In this state, the light emitting unit of the sensor unit 110 emits light, and the light receiving unit receives reflected light, whereby biological information, such as the pulse wave, is detected.

The biological information measurement apparatus 100 and the information processing apparatus 200 are connected by communication, thereby exchanging data. The information processing apparatus 200 is, for example, a mobile communication terminal, such as a smartphone, a mobile phone, or a future phone. Alternatively, the information processing apparatus 200 may be an information processing terminal, such as a tablet computer. As the communication connection of the biological information measurement apparatus 100 and the information processing apparatus 200, for example, proximity wireless communication, such as Bluetooth, may be used. In this way, the biological information measurement apparatus 100 and the mobile communication terminal 200 are connected by communication, whereby various kinds of biological information (first biological information, second biological information), such as the pulse rate and calorie consumption, can be displayed on a display unit 430 (LCD or the like) of the mobile communication terminal 200. That is, various kinds of information obtained based on the detection signal of the sensor unit 110 can be displayed. It should be noted that arithmetic processing of information, such as the pulse rate or calorie consumption, may be executed in the biological information measurement apparatus 100, and at least a part of the arithmetic processing may be executed in the mobile communication terminal 200.

It should be noted that the biological information measurement apparatus, the information processing apparatus, the biological information measurement system, and the like of the embodiment may realize a part or the most part of the processing by a program. In this case, a processor, such as a CPU, executes the program, thereby realizing the biological information measurement apparatus, the information processing apparatus, the biological information measurement system, and the like of the embodiment. Specifically, a program stored in a non-transient information storage device is read out, and the read program is executed by a processor, such as a CPU. Here, the information storage apparatus (computer-readable device) is stores a program, data, and the like, and the function thereof can be realized by an optical disc (DVD, CD, or the like), a hard disk drive (HDD), a memory (a card memory, a ROM, or the like), or the like. Then, the processor, such as a CPU, performs various kinds of information of the embodiment based on the program (data) stored in the information storage device. That is, the information storage device stores a program (a program for causing a computer to execute the processing of the respective units) for causing a computer (an apparatus including an operating unit, a processing unit, a storage unit, and an output unit) to function as the respective unit of the embodiment.

The biological information measurement apparatus, the information processing apparatus, the biological information measurement system, and the like of the embodiment may include a processor and a memory. The processor herein may be, for example, a central processing unit (CPU). However, the processor is not limited to the CPU, and various processors, such as a graphics processing unit (GPU) and a digital signal processor (DSP), may be used. The processor may be a hardware circuit by an application specific integrated circuit (ASIC). The memory stores computer-readable commands, and the commands are executed by the processor, thereby realizing the respective units of the biological information measurement apparatus, the information processing apparatus, the biological information measurement system, and the like of the embodiment. The memory herein may be a semiconductor memory, such as a static random access memory (SRAM) or a dynamic random access memory (DRAM), or may be a register, a hard disk, or the like. The commands herein may be commands of command sets of a program, or may be commands for instructing operation on hardware circuits.

As described above, although the embodiment has been described in detail, it can be understood by those skilled in the art that various modifications can be made without substantially departing from the new matters and the effect of the invention. Therefore, all modifications fall within the scope of the invention. For example, the terms used in the specification or the drawings at least once together with a different term having a broader or similar meaning can be replaced with the different term in any portion of the specification or the drawings. The configurations and operations of the biological information measurement apparatus, the information processing apparatus, and the biological information measurement system are not limited to those described in the embodiment, and various modifications may be made.

What is claimed is:

1. A biological information measurement apparatus comprising:
 a sensor unit;
 a processing unit which detects biological information, comprising first and second biological information, based on sensor information from the sensor unit;
 a communication unit which transmits the first and the second biological information to an information processing apparatus; and
 a time output unit which outputs time,
 wherein a delay time of transmission timing of the second biological information is calculated using identification information that is specific to the biological information measurement apparatus, wherein the communication unit obtains a first transmission timing based on the time output from the time output unit, and transmits the second biological information at a second transmission timing delayed from the first transmission timing by the calculated delay time.

2. The biological information measurement apparatus according to claim 1, further comprising:
 a storage unit which stores the second biological information corresponding to time information,
 wherein the communication unit transmits the second biological information stored in the storage unit at the second transmission timing.

3. The biological information measurement apparatus according to claim 1,
 wherein
 the communication unit transmits the first biological information in a first communication cycle and transmits the second biological information in a second communication cycle longer than the first communication cycle.

4. The biological information measurement apparatus according to claim 1, wherein the communication unit divides data of the second biological information into a plurality of blocks each having a plurality of packets and transmits the plurality of blocks.

5. The biological information measurement apparatus according to claim 4,
wherein the communication unit transmits the plurality of blocks with a first characteristic having a property of read with no acknowledge by proximity wireless communication and receives reception results of the blocks in the information processing apparatus with a second characteristic having a property of write with acknowledge.

6. The biological information measurement apparatus according to claim 1,
wherein the communication unit changes a communication speed from a first communication speed to a second communication speed faster than the first communication speed before transmitting the second biological information and changes the communication speed to a third communication speed slower than the second communication speed after the transmission of the second biological information is completed.

7. The biological information measurement apparatus according to claim 6,
wherein the communication unit receives a communication speed change instruction with a first characteristic having a property of write with acknowledge by proximity wireless communication, changes the communication speed based on the received communication speed change instruction, and transmits a communication speed change completion notification with a second characteristic having a property of read with acknowledge.

8. The biological information measurement apparatus according to claim 1,
wherein the communication unit transmits a notification that the second biological information is transmittable to the information processing apparatus at the second transmission timing when the second biological information is transmittable and transmits the second biological information when a transmission start instruction is received from the information processing apparatus.

9. The biological information measurement apparatus according to claim 8,
wherein the communication unit transmits an upload data size of the second biological information with a third characteristic having a property of read with acknowledge to the information processing apparatus to start the transmission of the second biological information when the transmission start instruction is received from the information processing apparatus.

10. The biological information measurement apparatus according to claim 1, further comprising:
a storage unit which stores the second biological information in association with a measurement time output from the time output unit at a timing when the second biological information is detected.

11. The biological information measurement apparatus according to claim 1,
wherein the first biological information includes information regarding at least one of a pulse, body temperature, blood pressure, a blood glucose level, a step count, and a calorie consumption.

12. The biological information measurement apparatus according to claim 1, wherein the second biological information includes information regarding at least one of calorie intake, mental stress information, behavior analysis information, and sleep information.

13. The biological information measurement apparatus according to claim 1,
wherein the second biological information is greater than the first biological information.

14. An information processing apparatus comprising:
a communication unit which:
performs communication with a biological information measurement apparatus, which detects biological information comprising first and second biological information based on sensor information from a sensor unit, and
obtains a first transmission timing of the first biological information; and
a processing unit,
wherein the communication unit receives the second biological information at a second transmission timing delayed from the first transmission timing by a delay time, wherein the delay time is calculated using identification information that is specific to the biological information measurement apparatus.

15. The information processing apparatus according to claims 14,
wherein the processing unit instructs the biological information measurement apparatus to start transmission of the biological information when the communication unit receives a notification that the biological information is transmittable from the biological information measurement apparatus.

16. The information processing apparatus according to claim 14,
wherein the communication unit receives the first biological information in a first communication cycle and transmits the second biological information in a second communication cycle longer than the first communication cycle.

17. The information processing apparatus according to the claim 14,
wherein the first biological information includes information regarding at least one of a pulse, body temperature, blood pressure, a blood glucose level, a step count, and calorie consumption.

18. The information processing apparatus according to claim 14,
wherein the second biological information, includes information regarding at least one of calorie intake, mental stress information, behavior analysis information, and sleep information.

19. A biological information measurement system comprising:
a biological information measurement apparatus; and
an information processing apparatus,
wherein the biological information measurement apparatus detects biological information, comprising first and second biological information, based on sensor information from a sensor unit, obtains a delay time of transmission timing of the second biological information calculated using identification information that is specific to the biological information measurement apparatus as input, and transmits the second biological information at a second transmission timing delayed from a first transmission timing, of the first biological information, by the calculated delay time, and the information processing apparatus receives the second biological information at the second transmission timing.

\* \* \* \* \*